US005986074A

United States Patent [19]
Marzilli et al.

[11] Patent Number: 5,986,074
[45] Date of Patent: Nov. 16, 1999

[54] METAL CHELATES AS PHARMACEUTICAL IMAGING AGENTS, PROCESSES OF MAKING SUCH AND USES THEREOF

[75] Inventors: Luigi G. Marzilli, Atlanta; Malgorzata Lipowska, Decatur; Lory Hansen; Andrew Taylor, Jr., both of Atlanta, all of Ga.

[73] Assignee: Emory University, Atlanta, Ga.

[21] Appl. No.: 08/993,219

[22] Filed: Dec. 18, 1997

Related U.S. Application Data

[63] Continuation-in-part of application No. 08/643,413, May 6, 1996, abandoned.

[51] Int. Cl.$^6$ .............................. C07F 13/00; C07F 15/00; C07F 3/00

[52] U.S. Cl. .................................. 534/14; 252/1; 424/1.1; 544/225; 544/226; 546/2; 546/6; 556/1; 556/42; 556/45; 556/57; 556/81; 556/113; 556/130; 556/137; 562/561

[58] Field of Search ............................... 424/1.1; 534/14; 252/1; 562/561; 556/1, 137, 42, 45, 57, 81, 113, 130; 546/2, 6; 544/225, 226

[56] References Cited

U.S. PATENT DOCUMENTS

| | | | |
|---|---|---|---|
| 4,849,511 | 7/1989 | Verbruggen | 534/14 |
| 4,925,650 | 5/1990 | Nosco et al. | 424/1.1 |
| 5,011,676 | 4/1991 | Thakur | 424/1.1 |
| 5,037,631 | 8/1991 | Nosco | 424/1.1 |
| 5,104,638 | 4/1992 | Nosco | 424/1.1 |
| 5,116,598 | 5/1992 | Nosco | 424/1.1 |
| 5,187,264 | 2/1993 | Verbruggen | 534/14 |
| 5,245,018 | 9/1993 | Kondo et al. | 534/14 |
| 5,268,163 | 12/1993 | Verbruggen | 424/1.1 |
| 5,308,603 | 5/1994 | Thakur | 424/1.49 |
| 5,419,905 | 5/1995 | Nosco | 424/1.65 |

FOREIGN PATENT DOCUMENTS

| | | |
|---|---|---|
| 0 173 424 A1 | 3/1986 | European Pat. Off. . |
| 0 250 013 B1 | 12/1987 | European Pat. Off. . |
| WO 92/05154 | 4/1992 | WIPO . |

OTHER PUBLICATIONS

Alazraki, N.P. et al., "Stress Thallium SPECT is Equally Effective for Predicting Outcomes for Women and Men in the Emory Angioplasty Versus Surgery Trial (East)," (1986) Soc. Of Nuclear Medicine 43$^{rd}$ Annual Meeting Abstract 53068.

Blaufox, M.D., "Procedures of Choice in Renal Nuclear Medicine," (1991) *J. Nuclear Medicine* 32(6):1301–1309.

Bubeck, B. et al., "Pharmacokinetics of Technetium–99m–MAG$_3$ in Humans," *J. Nuclear Medicine* (Aug. 1990) 31(8):1285–1293.

Dogan, A.S. and Kirchner, P.T., "Hepatobiliary Excretion of MAG3 Simulation of a Urinary Leak," (1993) *Clinical Nuclear Medicine* 18(9):746–750.

Eshima, D. et al., "Biological Studies on a New Class of Tc–99m Renal Tubular Function Agents," (1986) *Current Applications in Radiopharmacology* 237–247.

Eshima, D. et al., "Animal Evaluation of Technetium–99m Triamide Mercaptide Complexes as Potential Renal Imaging Agents," *J. Nuclear Medicine* (Jul. 1987) 28(7):1180–1186.

Eshima, D. and Taylor, A. Jr., "Technetium–99m ($^{99m}$Tc) Mercaptoacetyltriglycine: Update on the New $^{99m}$Tc Renal Tubular Function Agent," (1992) Seminars in Nuclear Medicine XXII(2):61–73.

Eshima, D. et al., "Evaluating the Role of Protein Binding on the Renal Extraction of Tc–99m Tubular Agents Utilizing an Isolated Perfused Rat Kidney Model," (1996) Society of Nuclear Medicine 43$^{rd}$ Annual Meeting Abstract 37990.

Eshima, D. et al., "Preparation and Evaluation of Tc–99m Sulfur Colloid for Lymphoscinitigraphy Studies," (1996) Society of Nuclear Medicine 43$^{rd}$ Annual Meeting Abstract 37987.

Halkar, R.K. et al., "Interoperator Variability in Quantitating the MAG3 Renal Uptake Based on Semiautomated and Manual Regions of Interest," (1996) Society of Nuclear Medicine 43$^{rd}$ Annual Meeting Abstract 53086.

Halkar, R.K. et al., "Coronary Collaterals and Reversibility in Stress/Rest Reinjection TL–201 Myocardial Images," (1996) Society of Nuclear Medicine 43$^{rd}$ Annual Meeting Abstract 53085.

Hansen, L. et al., "A Promising Renal Tubular Function Agent that Combiines the Structural Features of MAG$_3$ and EC," Proceedings of 43$^{rd}$ Annual Meeting, *J. Nuclear Medicine* (May 1996 Supplement) 37(5):17P.

Jafri, R.A. et al., "Technetium–99m MAG$_3$, A Comparison with Iodine–123 and Iodine–131 Orthoiodohippurate, in Patients with Renal Disorders," (1988) *J. Nuclear Medicine* 29(2):147–158.

Jones, M.E. et al., "Solid Phase Gastric Emptying T1/2 Measurements Using Two Data Points," (1996) Society of Nuclear Medicine 43$^{rd}$ Annual Meeting Abstract 39024.

Lipowska, M. et al., "Synthesis and Characterization of Rhenium(V) Oxo Complexes with a New Thio–Amide–Thiourea Ligand System. X–ray Crystal Structure of [1–Phenyl–3–[2–((2–thioacetyl)amino)ethyl]thioureato]oxorhenium(V)" *Inorg. Chem.* (1996) 35:4484–4489.

(List continued on next page.)

*Primary Examiner*—Porfirio Nazario Gonzalez
*Attorney, Agent, or Firm*—Greenlee, Winner and Sullivan, P.C.

[57] ABSTRACT

The present invention relates to novel metal chelates, exemplified as technetium-99m or rhenium chelates, and to the process of preparing such metal chelates from corresponding ligands. These ligands and their corresponding metal chelates are synthesized to have a cysteinylethylene (EC) structure, a monothiourea (MTU) structure, or a dithiourea (DTU) structure. The present invention further relates to a pharmaceutical composition comprising a metal chelate, for example, a $^{99m}$Tc-chelate, to the use of the composition for renal imaging and examination of renal function, and to a kit for preparing such a composition prior to use.

14 Claims, 14 Drawing Sheets

OTHER PUBLICATIONS

Lipowska, M. et al., "Rhenium(v) Oxo Complexes of Novel $N_2S_2$ Dithiourea (DTU) Chelate Ligands: Synthesis and Structural Characterization," *Inorganic Chemistry* (1996) 35(14):4228–4231.

Lipowska, M. et al., "A New Versatile Method for Creating Small $N_2S_2$ Ligands Linked to Targeting Components," Proceedings of $43^{rd}$ Annual Meeting, *J. Nuclear Medicine* (1996) 37(5):190P.

Lipowska, M. et al., "A New One–Step Ligand Synthesis for Preparing Easily Targeted Small Neutral Tc–99m $N_2S_2$ Complexes," Proceedings of $43^{rd}$ Annual Meeting, *J. Nuclear Medicine* (1996) 37(5):191P.

Marzilli, L.G. et al., "Linking Deprotonation and Denticity of Chelate Ligands. Rhenium (V) Oxo Analogues of Technetium–99m Radiopharmaceuticals Containing $N_2S_2$ Chelate Ligands," (1994) *Inorganic Chemistry* 33:4850–4860.

Russell, C.D. et al., "Comparison of Technetium–99m $MAG_3$ with Iodine–131 Hippuran by a Simultaneous Dual Channel Technique," (1988) *J. Nucl. Med.* 29:1189–1193.

Schaap, G.H. et al., "$^{99m}$Tc–MAG3: Dynamic studies in patients with renal disease," (1988) *Eur. J. Nucl. Med.* 14:28–31.

Shattuck, L.A. et al., "Evaluation of the Hepatobiliary Excretion of Technetium–99m–MAG3 and Reconstitution Factors Affecting Radiochemical Purity," *J. Nuclear Medicine* (Feb. 1994) 35(2):349–355.

Taylor, A. et al., "Comparison of Tc–99mO(N, N'–Ethylenedicysteine Isomers in Rats and in Normal Volunteers," (1996) Society of Nuclear Medicine $43^{rd}$ Annual Meeting Abstract 53089.

Taylor, A., Jr. et al., "Technetium–99m $MAG_3$ Kit Formulation: Preliminary Results in Normal Volunteers and Patients with Renal Failure," *J. Nuclear Medicine* (May 1988) 29(5):616–622.

Taylor, A. Jr. et al., "Comparison of Iodine–131 OIH and Technetium–99m $MAG_3$ Renal Imaging in Volunteers," (1986) *J. Nuclear Medicine* 27(6):795–803.

Taylor, A. Jr. et al., "Clinical Comparison of I–131 Orthoiodohippurate and the Kit Formulation of Tc–99m Mercaptoacetyltriglycine," (1989) *Radiology* 170(3):721–725.

Taylor, A. Jr. and Eshima, D., "Effects of Altered Physiologic States on Clearance and Biodistribution of Technetium–99m $MAG_3$, Iodine–131 OIH, and Iodine–125 Iothalamate," (1988) *J. Nuclear Medicine* 29(5):669–675.

Taylor, A. Jr. et al., "Evaluation of Tc–99m Mercaptoacetyltriglycine in Patients with Impaired Renal Function," (1987) *Radiology* 162:365–370.

Taylor, A. Jr. et al., "$^{99m}$Tc–$MAG_3$, a new renal imaging agent: Preliminary results in patients," (1987) *Eur. J. Nucl. Med.* 12:510–514.

VanNerom, C. et al., "Comparison of Renal Excretion Characteristics of Isomers L,L and D,D of Tc–99m Ethylenedicysteine," *J. Nuclear Medicine*, Proceedings of the $37^{th}$ Annual Meeting, p. 806.

Verbruggen, A.M. et al., "Technetium–99m–L,L–Ethylenedicysteine: A Renal Imaging Agent. I. Labeling and Evaluation in Animals," *J. Nuclear Medicine* (Apr. 1992) 33(4):551–557.

Verbruggen, A. et al., "Evaluation of the Diastereomers of Tc–99m–Mercaptoace–Tylglycyl–D–Alanylglycine (Tc–99m–D–MAGAG) in Primates," Proceedings of the $35^{th}$ Annual Meeting, *J. Nuclear Medicine* (May 1988) 29(5);909–910.

L- CEMA

D- CEMA

L-CEPIC

D-CEPIC

L- CEPZ

D-CEPZ

Cysteinylethylene (EC)-based ligands

Cysteinylethylene (EC)-based ligands

TATU-Ph

TATU-Ph-OCH₃

TATU-PhCl

TATU-CH₃

TATU-(Me)₂

TATU-pPhCOOH

TATU-mPhCOOH

TATU-PhOCH₃

TATU-EtCOOH

TATU-COOH

Monothiourea (MTU)-based ligand

TATU-hippuric acid (Me)₂-TATU-EtCOOH

TATU-GlyGly (Me)₂-TAPTU-EtCOOH

Monothiourea (MTU)-based ligand (Me)₂-TATU-hippuric acid (Me)₂-TAPTU-hippuric acid Glycylglycyl-$\beta$-propionyl-thiourea Monothiourea (MTU)-based ligand DTU-Ph DTU-PhOCH

DTU-CH₃

DTU-PhCOOH

DTU-EtCOOH

Dithiourea (DTU)-based ligands

DTU-COOH

Et-DTU-Ph (Me)$_2$-DTU-PhOCH$_3$

COOH-DTU-Ph

DTU-CH$_3$,EtCOOH

Dithiourea (DTU)-based ligands

Scheme 1

Scheme 2

Scheme 3

R: alkyl
-(CH)$_m$COOH
(o,m,p)-C$_6$H$_4$-X

X: H, Cl, OCH$_3$, COOH m: 0,1,2

Scheme 4

Scheme 5

METAL CHELATES AS PHARMACEUTICAL IMAGING AGENTS, PROCESSES OF MAKING SUCH AND USES THEREOF

This application is a continuation-in-part of application U.S. Ser. No. 08/643,413 filed May 6, 1996, now abandoned.

The invention was partially made with Government support under Grant No. ROI DK38842-09 awarded by the National Institutes of Health. The United States Government has certain rights in this invention.

FIELD OF THE INVENTION

The present invention relates generally to a metal chelate, exemplified as a technetium-99m or rhenium chelate, and to the process of preparing the metal chelate from a corresponding ligand. The present invention further relates to a pharmaceutical composition comprising the metal chelate, to the use of the composition for renal imaging, and to a kit for preparing such a composition prior to use.

BACKGROUND OF THE RELATED ART

For example, radionuclide studies of the kidney provide a simple noninvasive method of evaluating both total and individual renal function. Radioactively-labeled compounds are utilized for the examinations of patients, for example, to ascertain the shape and function of internal organs and to evaluate the presence and location of pathological processes in the body. For this purpose, a composition comprising the radiopharmaceutical is administered to the patient, for example, in the form of an injectable liquid. By means of suitable detection apparatus, e.g., a gamma camera, images can be obtained of, for example, the organ or the pathological process in which the radioactive compound [radiopharmaceutical] has been incorporated, by recording the emitted radiation.

Compounds which are generally used as radiopharmaceutical agents include inter alia iodine-131 ($^{131}$I), $^{131}$I-orthohippurate (OIH), $^{125}$I-iothalamate, and technetium-99m ($^{99m}$Tc) chelates [Eshima et al. (1992) Sem. Nucl. Med. 22: 61–73; Verbruggen, U.S. Pat. No. 4,849,511 (1989); Nosco et al., U.S. Pat. No. 4,925,6501]. To date, one of the most successful agents is considered to be $^{99m}$Tc mercaptoacetyltriglycine ($^{99m}$TC MAG3). However, although considered to be the renal imaging agent of choice [Cosgriff et al. (1992) Nucl. Med. Comm. 13: 580–585; Verbruggen et al. (1992) J. Nucl. Med. 33: 551–557], $^{99}$Tc MAG3 is still not considered to be an ideal renal imaging agent because there are problems associated with its use. For example, the plasma-protein binding of $^{99m}$Tc MAG3 is very high [Taylor et al. (1987) Radiology 162: 365–370; Bubeck et al. (1990) J. Nucl. Med. 31: 1285–1293], the clearance of $^{99m}$Tc MAG3 is only 50–60% that of OIH and it does not provide a direct measurement of effective renal plasma flow. Furthermore, a small percentage of $^{99m}$Tc MAG3 is transported into the small intestine via the hepatobiliary system in normal volunteers; this percentage increases in patients with renal failure and can lead to problems in image interpretation [Taylor et al. (1987) Contr. Nephrol. 56: 38–46; Taylor et al. (1988) J. Nucl. Med. 29: 616–622; and Dogan et al. (1988) J. Nucl. Med. 29: 616–622]. Increased hepatobiliary activity can also occur with suboptimal kit preparation [Shattuck et al. (1994) J. Nucl. Med. 35: 349–355]. These limitations have prompted a continued need for improved renal imaging agents.

The promising results of $^{99m}$Tc MAG3, a triamide mercaptide ($N_3S$) compound, led to the synthesis of a number of structural variations of the MAG3 molecule, including replacement of the mercaptoacetyl moiety or one of the three glycines with a variety of natural occurring amino acids. Many of these ligands, labeled with $^{99m}$Tc, were tested in mice. The most promising agents were tested in one or two baboons and a few volunteers. In general, these substitutions resulted in products which were inferior to $^{99m}$Tc MAG3 or resulted in diastereomers with one diastereomer comparable and the other considerably inferior [e.g., mercaptoacetylglycylalanylglycine (MAGAG) [Verbruggen (1988) J. Nucl. Med. 29: 909]to $^{99m}$Tc MAG3. Diastereomeric radiopharmaceuticals with markedly different biokinetics require HPLC purification and are not practical for routine clinical use.

Additional $N_3S$ ligands were synthesized in order to evaluate the effect of different terminal amino acids and the form of the anionic group on the renal elimination of the compound. $^{99m}$Tc mercaptoacetylglycylglycyl-L-alanine ($^{99m}$Tc MAG2-Ala), and both complexes of $^{99m}$Tc mercaptoacetylglycylglycyl-L-asparagine ($^{99m}$Tc MAG2-Asn) and $^{99m}$Tc mercaptoacetylglycylglycyl-L-glutamine ($^{99m}$Tc MAG2-Gin) were shown to provide promising characteristics as imaging agents [Eshima et al. (1987) J. Nucl. Med. 28: 1180–1186]. Another promising $N_3S$ type metal chelate, $^{99m}$Tc mercaptoacetyl-glycylglycyl-taurine, was found to be inferior to $^{99m}$Tc MAG3 in dogs.

It was observed [Verbruggen et al. (1990) In *Technetium and rhenium in chemistry and nuclear medicine* 3, (Nicolini M., Bandoli G., and Mazzi U. eds) Verona: Cortina International, pp. 445–452] that the polar metabolite, $^{99m}$Tc L,L-ethylenedicysteine ($^{99m}$Tc LL-EC), of the brain agent, $^{99m}$Tc-L,L-ethylenedicysteine diethylester, was rapidly and efficiently excreted into the urine in mice; this observation led to the evaluation of $^{99m}$Tc LL-EC as a renal imaging agent. Studies in mice and baboons showed that the pharmacokinetic properties of $^{99m}$Tc LL-EC more closely approached those of OIH than the properties of MAG3 and also suggested that LL-EC was superior to the enantiomer $^{99m}$Tc DD-EC [Verbruggen et al. (1992) supra; Van Nerom et al. (1990) J. Nucl. Med. 31: 806; Van Nerom et al. (1994) In *Radionuclides in nephrology*, Blue Bell, Pa.: Field & Wood Medical Periodicals, pp. 13–20].

An ideal, improved $^{99m}$Tc complex would be expected to possess a renal clearance that exceeds the clearance of $^{99m}$Tc MAG3 by almost 100% in order to approach the clearance of OIH. Such an ideal metal complex could even exceed the clearance of OIH, since the clearance of OIH is only 83% of the clearance of p-aminohippuric acid (PAH), the gold standard for effective renal plasma flow (ERPF) [Bubeck et al. (1990) J. Nucl. Med. 31: 1285–1293]. Not only would a second generation agent provide a better measure of ERPF, the higher clearance would be expected to result in an improved kidney to background ratio and more rapid excretion than MAG3; these features would be expected to result in improved diagnostic studies particularly in neonates, patients with azotemia and patients with suspected obstruction just as the higher clearance of MAG3 compared to DTPA significantly enhanced the diagnostic utility of radionuclide renography in these patient populations.

Thus, there exists a need for a suitable composition for examining renal function comprising a labeled metal chelate which is readily available and easily prepared prior to use, especially in critical circumstances, e.g., in particular for kidney transplantation patients, accident victims and patients after large vascular operations.

There also exists a need for a suitable composition for examining renal function comprising a labeled metal chelate which shows specificity for the organ under examination, e.g., kidney.

3

There exists a need for a suitable composition for examining renal function, which comprises a labeled metal chelate that does not constitute a serious radiation burden for the patient and that does not have to be administered to the patient only in restricted doses, and which, consequently, does not result in obtaining insufficient information to obtain statistically reliable images of the renal function.

There exists a need for a suitable composition for examining the renal function which comprises a labeled metal chelate that does not present the problem of restricted availability due to too short a half-life and thus precluding the thorough and accurate completion of a renal examination with the metal chelate radionuclide as imaging agent.

There exists a need for a suitable composition for examining the renal function comprising a labeled metal chelate that is capable of being prepared prior to use from a kit formulation in order to maximize the life and stability of the renal imaging composition. The general availability of a ready-to-use labeled product suitable for organ imaging is precluded by the relatively short half-life of radionuclides used in the preparation of imaging agents. Thus, it is desirable to provide an easy and simple procedure for the preparation of a labeled metal chelate just prior to use and conveniently at the place of use. Preferably, it is desirable to provide a kit comprising reaction components necessary for - situ labeling of a ligand precursor, thereby enabling the preparation of a corresponding metal chelate prior to its use as an imaging agent.

SUMMARY OF THE INVENTION

It is an object of the invention to provide a metal chelate suitable as a pharmaceutical agent for renal imaging and examination of renal function. The metal chelate of the invention has a high organ-specificity, possesses a sufficient stability to permit completion of the preparation and thorough performance of a renal examination and that is amenable to a kit formulation whereby the metal chelate of the invention can be easily and simply prepared prior to use for renal imaging and examination.

In particular embodiments of the invention, a metal chelate based on a cysteinyl ethylene (CE) structure is provided as being suitable as a pharmaceutical agent and as having the general formula (I)

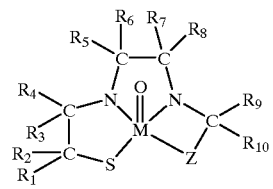

wherein $R_1$–$R_{10}$ are individually selected from the group consisting of hydrogen, a straight or branched, unsubstituted or substituted alkyl having C=1–4, and ACOOH wherein A is a straight, unsubstituted or substituted alkyl group having C=0–4;

$R_3$ together with $R_4$, $R_5$ together with $R_6$, $R_7$ together with $R_8$, and $R_9$ together with $R_{10}$ may form an oxygen atom;

4

Z is selected from the group consisting of

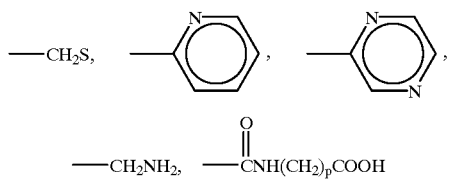

where p=1–3, and
—$CH_2NH(CH_2)_pCOOH$ where p=1–3; and
M is selected from the group consisting of Tc, Re, Cd, Pb, Zn, Hg, Ag, Au, Ga, Pt, Pd, Rh, Cr and V;
with the provision that
(a) at least one of $R_1$–$R_{10}$ is ACOOH or, together with one other R group, forms an oxygen atom; and/or
(b) only one of $R_1$, $R_2$, $R_3$ or $R_4$ and $R_5$, $R_6$, $R_7$ or $R_8$ and $R_9$ or $R_{10}$ is a straight or branched, unsubstituted or substituted alkyl of $C_3$ or $C_4$ or is an ACOOH wherein A is a straight or branched, unsubstituted or substituted alkyl group having C=0–4.

In particular embodiments, the cysteinylethylene-based metal chelate variants, satisfying the above general formula (1), were synthesized as metal (technetium and/or rhenium) chelates and tested for renal clearance. For example, L- and/or D-isomers of the metal chelates cysteinylethylenemercaptoacetamide (CEMA), cysteinylethylenepyridine carboxamide (CEPIC), cysteinylethylene-pyrazine is carboxamide (CEPZ), cysteinylethyleneglycine (CEG), thiodiacetamide-amine-$CH_3$ (TDAA—$CH_3$), thiodiacetamide-amine-$CH_2CH_2COOH$ (TDM—$CH_2CH_2COOH$) and cysteinylacetylglycylglycine ($CAG_2$) represent some of the compounds having the general formula (I) that have been chemically synthesized and tested for renal clearance.

In a particular embodiment of this invention, the technetium and rhenium chelates of L-CEMA and of D-CEMA exhibited a significantly superior renal clearance when compared to MAG3 in rats. In other embodiments, the renal clearance of DD-$^{99m}$Tc-ethylenedicysteine (DD-EC) was shown to be significantly higher than that of its LL-isomer and than that of $^{99m}$Tc MAG3 in rats. $^{99m}$Tc-CEPIC exhibited rat renal clearance efficiency similar to that of $^{99m}$Tc MAG3.

In other embodiments of the invention, a metal chelate based on a monothiourea (MTU) structure and suitable as a pharmaceutical agent has the general formula (II)

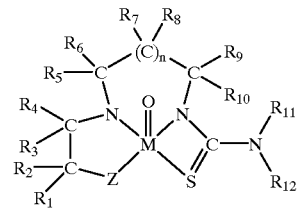

wherein
n=0 or 1,
$R_1$–$R_{12}$ are individually selected from the group consisting of hydrogen, a straight or branched, unsubstituted or substituted alkyl having C=1–4, and ACOOH wherein A is a straight or branched, unsubstituted or substituted alkyl group having C=0–4;

$R_1$ together with $R_2$, $R_3$ together with $R_4$, and $R_5$ together with $R_6$ may form an oxygen atom;

$R_{11}$ and $R_{12}$ may alternatively be selected individually from the group consisting of

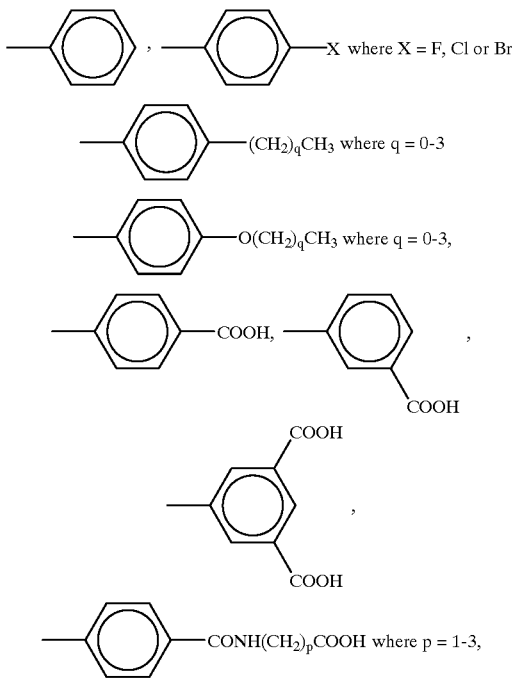

—$(CH_2)_p COOH$ where p=0 or 2, and
—$CH_2CONH(CH_2)_p COOH$ where p=1–3;
Z is selected from the group consisting of S and $N(CH_2)_p COOH$ where p=1–3; and
M is selected from the group consisting of Tc, Re, Cd, Pb, Zn, Hg, Ag, Au, Ga, Pt, Pd, Rh, Cr and V;
with the provision that
(a) at least one of $R_1$–$R_{10}$ is ACOOH or, together with one other R group, forms an oxygen atom; and/or
(b) only one of $R_1$, $R_2$, $R_3$ or $R_4$ and $R_5$, $R_6$, $R_7$ or $R_8$ and $R_7$, $R_8$, $R_9$ or $R_{10}$ is a straight or branched, unsubstituted or substituted alkyl of $C_3$ or $C_4$ or is an ACOOH wherein A is a straight or branched, unsubstituted or substituted alkyl group having C=0–4.

Various monothiourea (MTU)-based metal-containing compounds satisfying the above general formula (II) were synthesized as $^{99m}$Tc and/or Re chelates and tested for renal clearance. For example, chemical structures such as thioacetamidethiourea-phenyl (TATU-Ph), thioacetamidethiourea-phenylmethoxy (TATU-PhOCH$_3$), thioacetamidethiourea-phenylchloro (TATU-PhCl), thioacetamidethiourea-methyl (TATU-CH$_3$), thioacetamidethiourea-dimethyl (TATU-(Me)$_2$), thioacetamidethiourea-para-phenylCOOH (TATU-pPhCOOH), thioacetamidethiourea-meta-phenylCOOH (TATU-mPhCOOH), thioacetamidethiourea-meta-phenyl (COOH)$_2$ (TATU-mPh(COOH)$_2$), thioacetamidethiourea-ethylCOOH (TATU-EtCOOH), thioacetamidethiourea-carboxylic acid (TATU-COOH), thioacetamidethiourea-hippuric acid (TATU-hippuric acid), thioacetamidethiourea-glycylglycine (TATU-GlyGly), dimethylthioacetamidethiourea-ethylCOOH ((Me)$_2$-TATU-EtCOOH), dimethylthioacetamidethiourea-hippuric acid ((Me)$_2$-TATU-hippuric acid), dimethylthioacetamidepropylthiourea-ethylCOOH ((Me)$_2$-TAPTU-EtCOOH), dimethylthioacetamidepropylthiourea-hippuric acid ((Me)$_2$-TAPTU-hippunc acid) and glycylglycyl-β-propionyl-thiourea (TPG$_2$ represent some of the compounds having the general formula (II) that have been chemically synthesized as technetium and/or rhenium chelates for use as pharmaceuticals suitable for examination of renal function.

In a specific embodiment of the invention, the thioacetamidethiourea-ethylCOOH (TATU-EtCOOH) metal chelate with technetium or rhenium, in particular, exhibited superior renal clearance in rats when compared to a corresponding MAG3 metal chelate. Thioacetamidethiourea-pPhCOOH (TATU-pPh) was cleared at a moderate rate. Also, it was observed that dimethyl-thioacetamide propylthiourea-ethylCOOH ((Me)$_2$-TAPTU-EtCOOH) exhibited greater stability than the corresponding thioacetamide-thiourea derivative.

In additional embodiments of the invention, a metal chelate based on a dithiourea (DTU) structure and suitable as a pharmaceutical agent has the general formula (III)

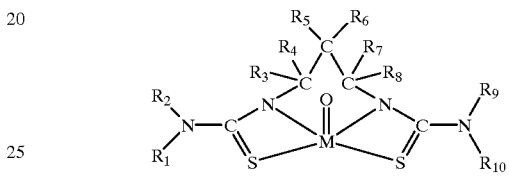

wherein
$R_1$–$R_{10}$ are individually selected from the group consisting of hydrogen, a straight or branched, unsubstituted or substituted alkyl having C=1–4, and ACOOH wherein A is a straight or branched, unsubstituted or substituted alkyl group having C=0–4;
$R_1$, $R_2$, $R_9$ and $R_{10}$ may alternatively be selected individually from the group consisting of

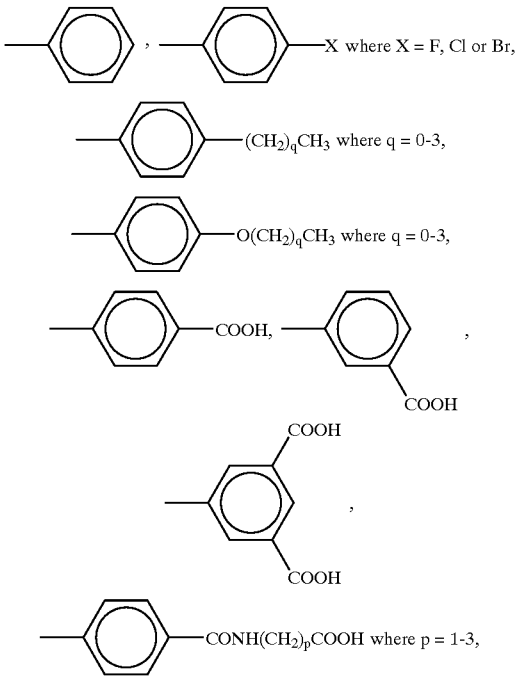

—$(CH_2)_p COOH$ where p=0 or 2, and
—$CH_2CONH(CH)_p COOH$ where p=1–3; and
M is selected from the group consisting of Tc, Re, Cd, Pb, Zn, Hg, Ag, Au, Ga, Pt, Pd, Rh, Cr and V;

with the provision that only one of $R_1$ or $R_2$, and $R_3$, $R_4$, $R_5$, or $R_6$, and $R_5$, $R_6$, $R_7$ or $R_8$, and $R_9$, or $R_{10}$ is a straight or branched, unsubstituted or substituted alkyl of $C_3$ or $C_4$, or is an ACOOH wherein A is a straight or branched, unsubstituted or substituted alkyl group having C=0–4.

Various dithiourea (DTU)-based metal-containing compounds satisfying the above general formula (III) were synthesized as $^{99m}Tc$ and/or Re chelates and tested for renal clearance. For example, chemical structures such as dithiourea-phenyl (DTU-Ph), dithiourea-phenylmethoxy (DTU-PhOCH$_3$), dithiourea-methyl (DTU-CH$_3$), dithiourea-phenylCOOH (DTU-PhCOOH), dithiourea-ethylCOOH (DTU-EtCOOH), dithiourea-carboxylic acid (DTU-COOH), ethyldithiourea-phenyl (Et-DTU-Ph), dimethyl-dithiourea-phenylmethoxy ((Me)$_2$-DTU-PhOCH3), carboxyl-dithiourea-phenyl (COOH-DTU-Ph), and methyl-dithiourea-ethylCOOH (Me-DTU-EtCOOH) represent some of the compounds having the general formula III that have been chemically synthesized as technetium and/or rhenium chelates for use as radiopharmaceuticals suitable for examination of renal function.

It is a further object of the present invention to provide an organic molecule (ligand) capable of tightly chelating with a nuclide to form a metal chelate suitable as a pharmaceutical agent for renal imaging and examination of renal function.

Particular embodiments of the invention provide ligands suitable for the formation of metal chelates having the structural formulae (I), (II) or (III). A ligand useful for preparation of a metal chelate of formula (I), (II) or (III) possesses a corresponding chemical structure satisfying, respectively, the general formula (IV)

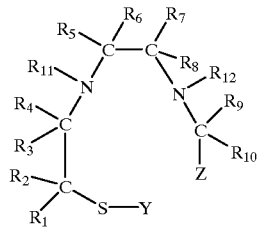

wherein $R_1$–$R_{12}$ are individually selected from the group consisting of hydrogen, a straight or branched, unsubstituted or substituted alkyl having C=1–4, a hydroxy-alkyl, and ACOOH wherein A is a straight or branched, unsubstituted or substituted alkyl group having C=0–4;

$R_3$ together with $R_4$, $R_5$ together with $R_6$, $R_7$ together with $R_8$, and $R_9$ together with $R_{10}$ may form an oxygen atom;

Z is selected from the group consisting of

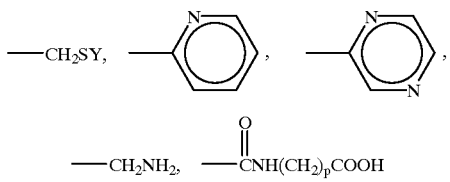

where p=1–3, and

—CH$_2$NH(CH$_2$)$_p$COOH where p=1–3; and

Y is a hydrogen atom or a suitable protecting group;
with the provision that (a) at least one of $R_1$–$R_{10}$ is ACOOH or, together with one other R group, forms an oxygen atom; and/or (b) only one of $R_1$, $R_2$, $R_3$ or $R_4$ and $R_5$, $R_6$, $R_7$ or $R_8$ and $R_9$ or $R_{10}$ is a straight or branched, unsubstituted or substituted alkyl of $C_3$ or $C_4$, a hydroxy-alkyl, or is an ACOOH wherein A is a straight or branched, unsubstituted or substituted alkyl group having C=0–4;

or the general formula (V)

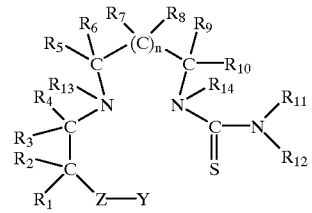

wherein n=0 or 1, $R_1$–$R_{14}$ are individually selected from the group consisting of hydrogen, a straight or branched, unsubstituted or substituted alkyl having C=1–4, a hydroxy-alkyl, and ACOOH wherein A is a straight or branched, unsubstituted or substituted alkyl group having C=0–4;

$R_1$ together with $R_2$, $R_3$ together with $R_4$, and $R_5$ together with R may form an oxygen atom;

$R_{11}$ and $R_{12}$ may alternatively be selected individually from the group consisting of

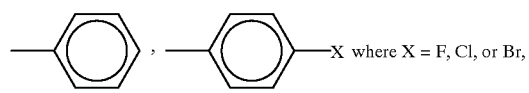

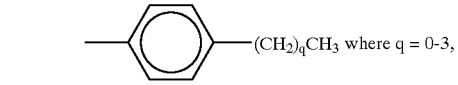

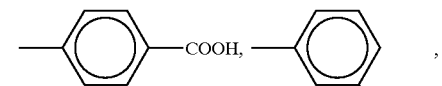

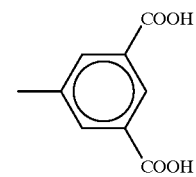

—(CH$_2$)$_p$COOH where p=0 or 2; and

—CH$_2$CONH(CH)$_p$COOH where p=1–3;

Z is selected from the group consisting of S and N(CH$_2$)$_p$COOH where p=1–3; and Y is a hydrogen or a suitable protecting group;

with the provision that (a) at least one of $R_1$–$R_{10}$ is ACOOH or, together with one other R group, forms an oxygen atom; and/or (b) only one of $R_1$, $R_2$, $R_3$ or $R_4$ and $R_5$, $R_6$, $R_7$ or $R_8$ and $R_7$, $R_8$, $R_9$ or $R_{10}$ is a straight or branched, unsubstituted or substituted alkyl of $C_3$ or $C_4$, a hydroxy-alkyl, or is an ACOOH wherein A is a straight or branched, unsubstituted or substituted alkyl group having C=0–4. or the general formula (VI)

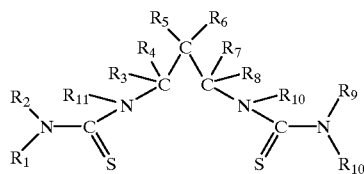

wherein $R_1$–$R_{12}$ are individually selected from the group consisting of hydrogen, a straight or branched, unsubstituted or substituted alkyl having C=1–4, a hydroxy-alkyl, and ACOOH wherein A is a straight or branched, unsubstituted or substituted alkyl group having C=0–4;

$R_1$, $R_2$, $R_9$ and $R_{10}$ may alternatively be selected individually from the group consisting of

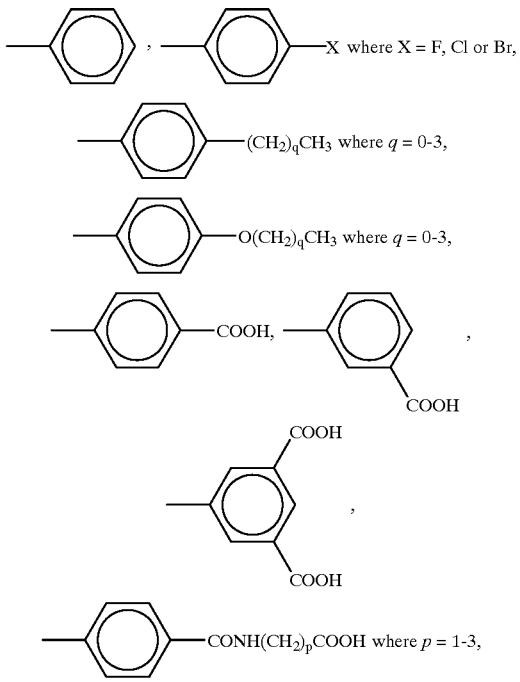

—(CH)$_p$COOH where p=0 or 2, and
—CH$_2$CONH(CH$_2$)$_p$COOH where p=1–3;
with the provision that only one of $R_1$ and $R_2$, and $R_3$, $R_4$, $R_5$, or $R_6$, and $R_5$, R6, $R_7$ or $R_8$, and $R_9$ is a straight or branched, unsubstituted or substituted alkyl of $C_3$ or $C_4$, a hydroxy-alkyl, or is an ACOOH wherein A is a straight or branched, unsubstituted or substituted alkyl group having C=0–4.

This invention further contemplates that ligands satisfying the general formulae (IV), (V) or (VI) are capable of forming metal chelates with nuclides including, but not limited to technetium, rhenium, cadmium, lead, zinc, mercury, silver, gold, gallium, platinum, palladium, rhodium, chromium, vanadium and the like. Methods are provided by this invention for the chelation process between a nuclide and a ligand having a chemical formula (IV), (V) or (VI) to form a metal chelate having a chemical structure specified by general formula (I), (II) or (III). Particular embodiments describe methods used for the interaction between the ligands of the invention and technetium and/or rhenium to form $^{99m}$Tc-chelates and Re(V)-chelates useful as radiopharmaceutical agents for renal imaging and examination of renal function. It is further contemplated by this invention that the ligands of the invention can be chelated with nuclides including, but not limited to, Tc, Re, Cd, Pb, Zn, Hg, Ag, Au, Ga, Pt, Pd, Rh, Cr and V to form metal chelates which can be utilized as inhibitor agents, for example, for inhibiting metalloenzymes, as chelating agents, for example, for chelating toxic metals, and the like.

The present invention also provides a method for the chemical synthesis of a ligand which can be used to tightly chelate a nuclide to form a metal chelate suitable as a pharmaceutical agent. In a particular embodiment of this invention, a cysteinylethylene (CE)-based ligand having a structure defined by formula (IV) is synthesized by a method comprising modification of the ethylenecysteine structure. In another embodiment, a previously unknown monothiourea (MTU)-based ligand having a structure defined by formula (V) is synthesized by combining thiourea into a multidentate ligand and therein establishing a new class of ligands. In addition, yet another previously unknown dithiourea (DTU)-based ligand having a structure satisfied by formula (VI) is synthesized by a method in which two thiourea moieties are incorporated into a multidentate system and thereby establishing a new class of ligands.

Further, this invention provides a pharmaceutical composition useful for renal imaging and examination of renal function in humans and other mammals. Such a pharmaceutical composition comprises a metal chelate of the invention and a pharmaceutically acceptable carrier.

In addition, this invention provides a kit comprising the chemical reagents necessary for the chelation of a suitable radionuclide with a ligand of the invention to prepare, immediately prior to use, a metal chelate and a radiopharmaceutical composition thereof for use in renal imaging and examination of renal function.

DETAILED DESCRIPTION OF THE INVENTION

Figure 1A:
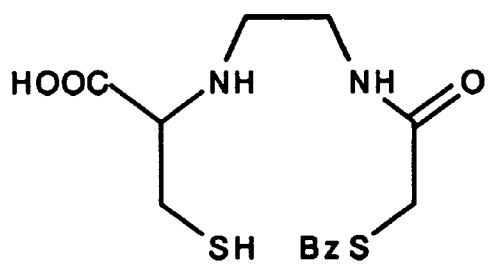
FIGS. 1A–1B present some examples of cysteinylethylene (CE)-based ligands that are defined by the general formula (IV).
Figure 1A:
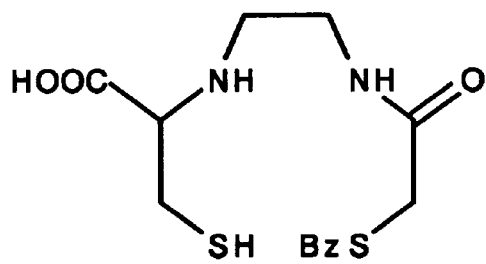
Figure 1A:
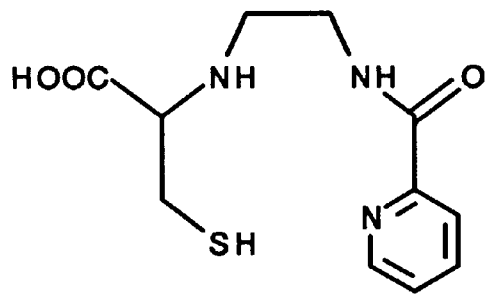
Figure 1A:
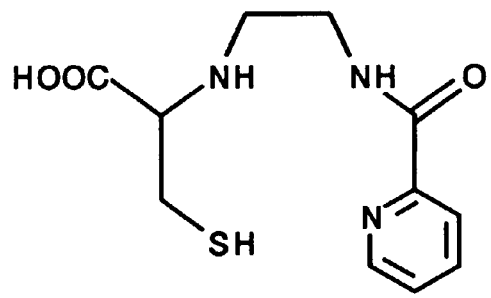
Figure 1A:
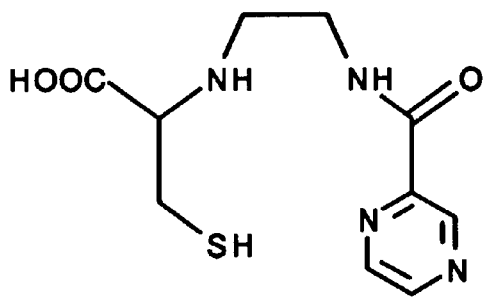
Figure 1A:
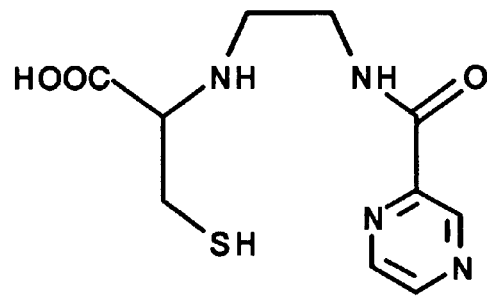
Figure 1B:
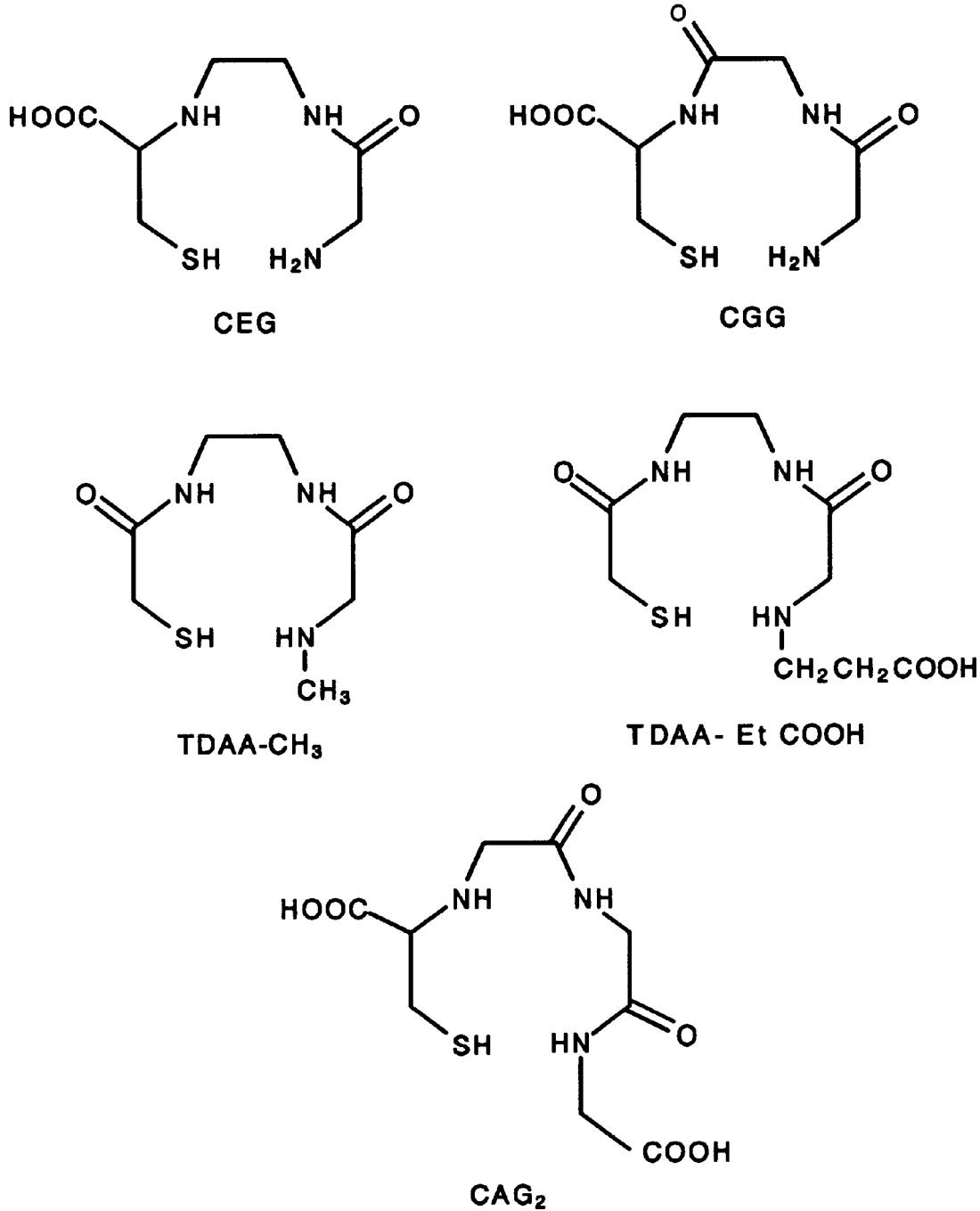
Figure 2A:
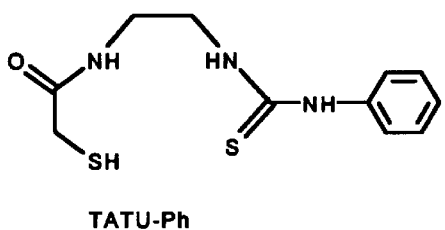
FIGS. 2A–2C present some examples of monothiourea (MTU)-based ligands that are defined by the general formula (V).
Figure 2A:
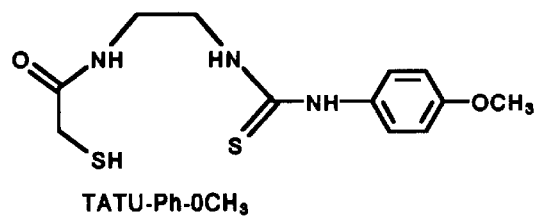
Figure 2A:
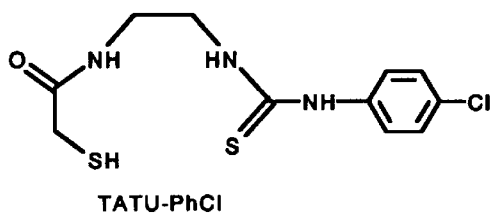
Figure 2A:
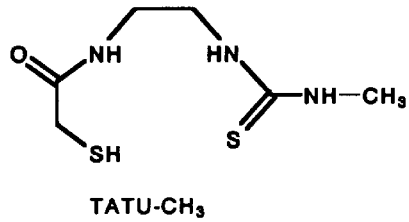
Figure 2A:
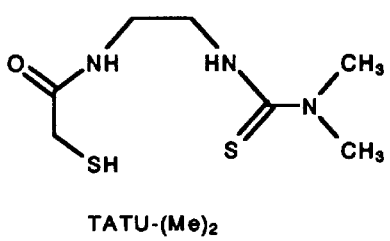
Figure 2A:
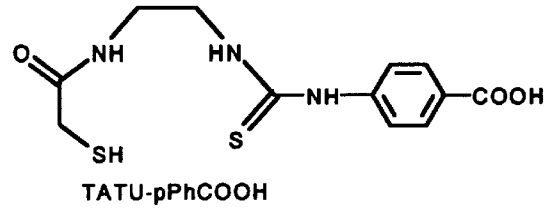
Figure 2A:
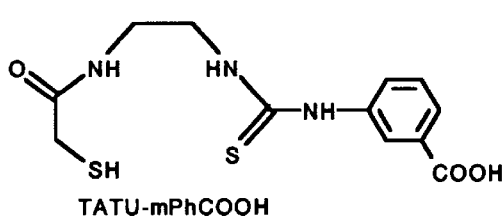
Figure 2A:
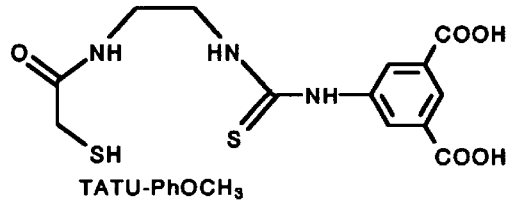
Figure 2A:
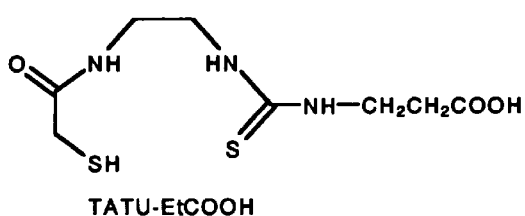
Figure 2A:
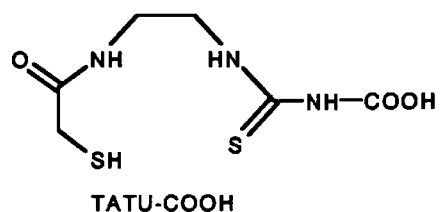
Figure 2B:
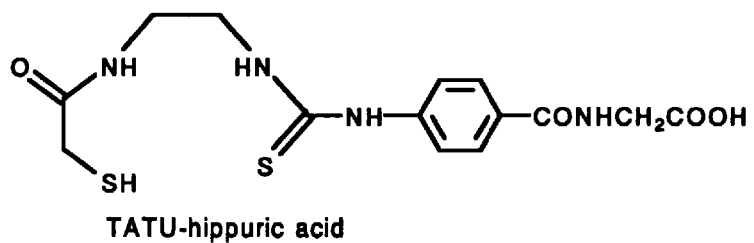
Figure 2B:
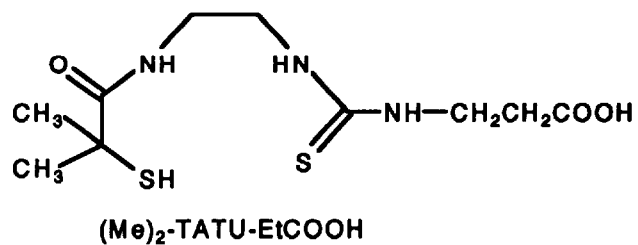
Figure 2B:
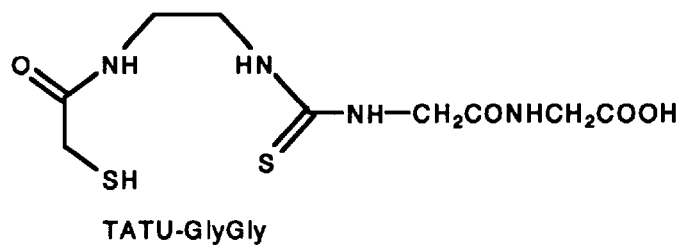
Figure 2B:
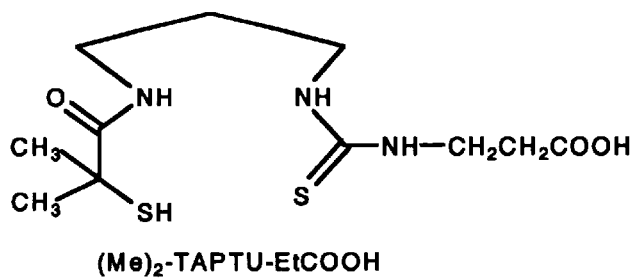
Figure 2C:
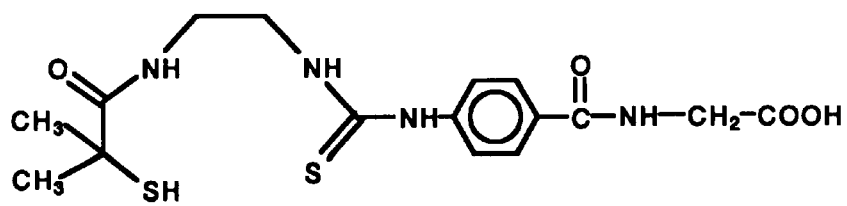
Figure 2C:
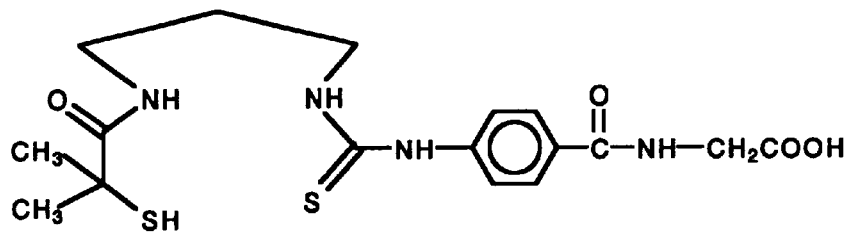
Figure 2C:
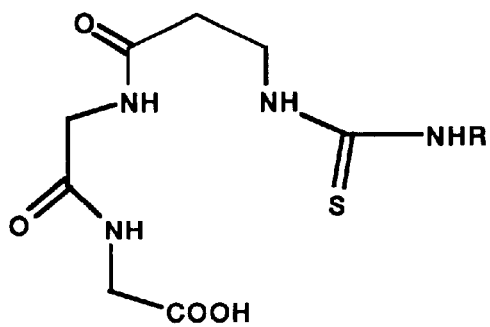
Figure 3A:
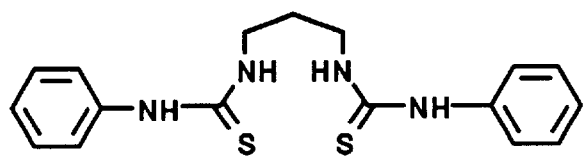
FIGS. 3A–3B present some examples of dithiourea (DTU)-based ligands that are defined by the general formula (VI).
Figure 3A:
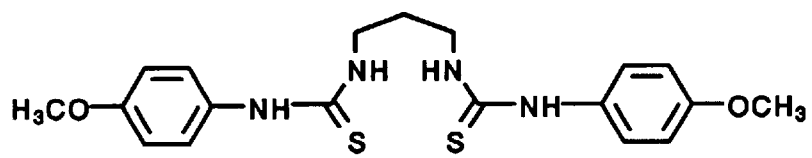
Figure 3A:
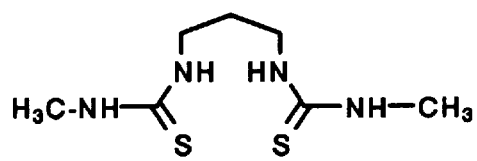
Figure 3A:
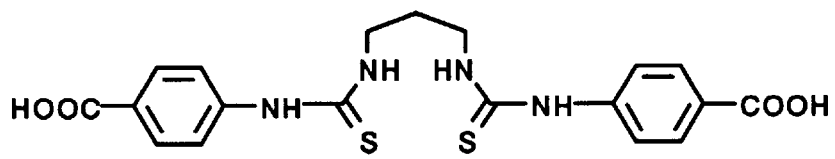
Figure 3A:
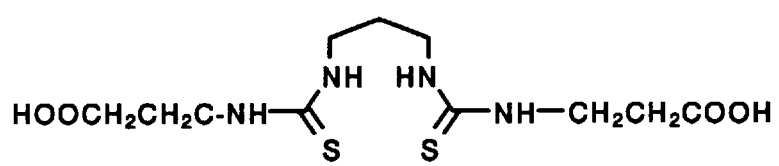
Figure 3B:
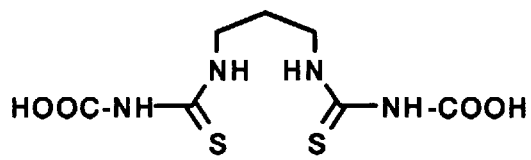
Figure 3B:
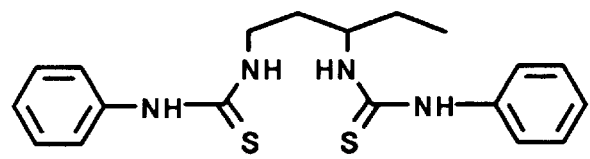
Figure 3B:
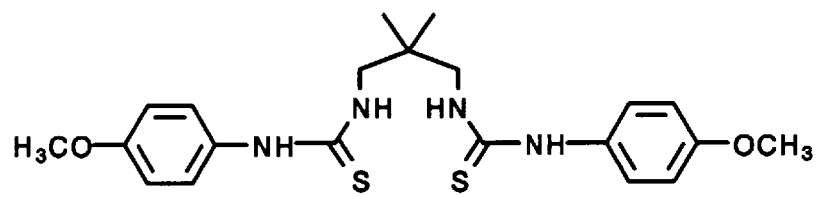
Figure 3B:
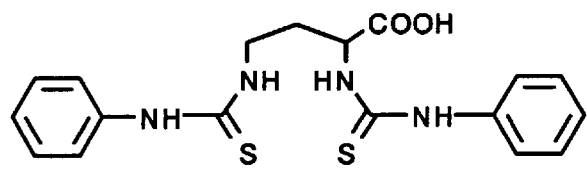
Figure 3B:
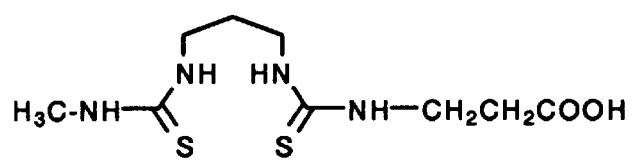

The present invention is directed to novel metal chelate compounds that are suitable candidates for use as pharmaceutical imaging agents in renal function examinations. More particularly, the invention is directed to organic molecules chelated to nuclides including, but not limited to, Tc, Re, Cd, Pb, Zn, Hg, Ag, Au, Ga, Pt, Pd, Rh, Cr, V and, most particularly, to Tc and Re chelates.

In one embodiment of the invention is provided a metal chelate based on cysteinylethylene (CE) structure and having the general formula (I)

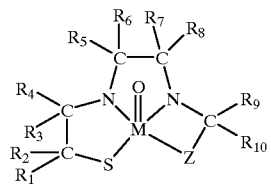

wherein $R_1$–$R_{10}$ are individually selected from the group consisting of hydrogen, a straight or branched, unsubstituted or substituted alkyl having C=14, and ACOOH wherein A is a straight, unsubstituted or substituted alkyl group having C=0–4;

$R_3$ together with $R_4$, $R_5$ together with $R_6$, $R_7$ together with $R_8$, and $R_9$ together with $R_{10}$ may form an oxygen atom;

Z is selected from the group consisting of

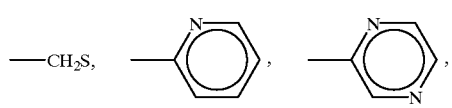

—continued

—$CH_2NH_2$, —$\overset{O}{\overset{\|}{C}}NH(CH_2)_pCOOH$ where p=1–3, and

—$CH_2NH(CH)_pCOOH$ where p=1–3; and

M is selected from the group consisting of Tc, Re, Cd, Pb, Zn, Hg, Ag, Au, Ga, Pt, Pd, Rh, Cr and V;

with the provision that (a) at least one of $R_1$–$R_{10}$ is ACOOH or, together with one other R group, forms an oxygen atom; and/or (b) only one of $R_1$, $R_2$, $R_3$ or $R_4$ and $R_5$, $R_6$, $R_7$ or $R_8$ and $R_7$, $R_8$, $R_9$ or $R_{10}$ is a straight or branched, unsubstituted or substituted alkyl of $C_3$ or $C_4$, or is an ACOOH wherein A is a straight or branched, unsubstituted or substituted alkyl group having C=0–4.

This group of metal chelates is exemplified in particular by structural formulae of $^{99m}$Tc chelates based on a cysteinylethylene structure as illustrated in FIG. 1, i.e., L- and D-cysteinylethylenemercaptoacetamide (L-CEMA and D-CEMA), L- and D-cysteinylethylenepyridine carboxamide (L-CEPIC and D-CEPIC), L-cysteinylethylenepyrazine carboxamide (L-CEPZ), cysteinylethyl-enylglycine (CEG), thiodiacetamide-amine-$CH_3$ (TDAA-$CH_3$), thiodiacetamide-amine-$CH_2CH_2COOH$ (TDAA-$CH_2CH_2COOH$) and cysteinyl-acetylglycylglycine ($CAG_2$).

L-CEMA, D-CEMA and L-CEPIC were tested for renal clearance in rats. Table 1 clearly shows the rapid and selective removal of the test compounds by the kidneys, with only trace amounts being taken up in other major organs. This is an important feature of an imaging agent so as to avoid damage to body tissues from radiation emitted by the radiolabel, and so as to minimize the amount of radiopharmaceutical required to be administered in order to obtain a suitable image.

TABLE 1

BIODISTRIBUTION RESULTS* IN NORMAL RATS

| | Test Compound | | | | | |
|---|---|---|---|---|---|---|
| Organ | $^{99m}$Tc L-CEMA* | $^{99m}$Tc D-CEMA** | $^{99m}$Tc L-CEPIC** | $^{99m}$Tc MAG3*** | $^{99m}$Tc D,D-EC*** | $^{99m}$Tc L,L-EC*** |
| Liver | 2.2 | 4.7 | 4.8 | 1 | 2.9 | 4.5 |
| Intestines | 2.7 | 4.0 | 6.4 | 5 | 2.6 | 1.8 |
| Stomach | ~1.0 | <1 | 1.9 | <1 | <1 | <1 |
| Kidneys | 6.8 | 3.4 | 7.2 | 23 | 5.4 | 24.4 |
| Bladder | 72.2 | 74.5 | 58.2 | 57 | 63.2 | 45.6 |
| Carcass | 15.0 | 13.1 | 19.8 | 14 | 25.4 | 22.6 |

*Results are presented as percent of total activity. >1% is found in spleen, heart and lung.
**30 minutes post injection.
***22 minutes post injection.

Notably, it is shown in Table 1 that $^{99m}$TcL-CEMA, $^{99m}$Tc-D-CEMA and $^{99m}$Tc-CEPIC are even more rapidly excreted by the kidneys than $^{99m}$Tc MAG3. Further, it is demonstrated in Table 1 that $^{99m}$TcD,D-EC also exhibits a more rapid renal clearance than $^{99m}$Tc MAG3 and that, unexpectedly, $^{99m}$Tc-D,D-EC is superior to L,L-EC in rats and probably also in humans.

A comparison between different configurations of $^{99m}$TcO-CEMA and OIH is presented in Table 2. As shown in Table 2, syn-L-CEMA and syn-D-CEMA showed higher clearance than the corresponding anti forms, despite greater plasma protein binding. Also, the syn forms of CEMA exhibited higher clearance than the anti forms with the syn-L-CEMA clearance rate approaching that of OIH. With respect to extraction efficiency, L-CEMA was equal to or slightly superior to OIH.

TABLE 2

Renal Plasma Clearance, Extraction Efficiency (EE) and Plasma Protein Binding (PPB) of $^{99m}$TcO-CEMA in Rats (n = 6): Comparison with OIH

| | Clearance (ml/min/100 g) | Clearance Ratio Tc/OIH (%) | EE % | EE Ratio Tc/OIH (%) | PPB % |
|---|---|---|---|---|---|
| anti-L-CEMA | 2.25 ± 0.25 | 85 ± 3 | 68 ± 4 | 105 ± 10 | 68 ± 4 |
| syn-L-CEMA | 2.89 ± 0.69 | 93 ± 11 | 76 ± 7 | 102 ± 10 | 78 ± 8 |
| anti-D-CEMA | 1.27 ± 0.52 | 41 ± 17 | 44 ± 18 | 57 ± 22 | 81 ± 6 |
| syn-D-CEMA | 1.77 ± 0.19 | 65 ± 10 | 62 ± 8 | 89 ± 10 | 96 ± 1 |

Anti and syn configurations as in Marzille et al. (1994) Inorg. Chem. 33(22):4850–4860

In humans, the clearance rate (EC/OIH) was 82±8% for DD-EC compared to EZ 70±3% and 40±5% for LL-EC and DL-EC, respectively. DD and LL-EC were excreted at essentially the same rate in the urine; DL-EC had a slower rate of excretion. A potential limitation of both $^{99m}$Tc DD- and LL-EC is the fact that they exist in dianionic (80%) and monoanionic (20%) forms at physiological pH and it is unlikely that these two forms have the same clearance or protein binding affinity; nevertheless, $^{99m}$Tc DD-EC has excellent imaging properties and its clearance may approach that of OIH more closely than any other $^{99m}$Tc renal agent (Taylor et al. (1996) Abstract 53089, Society of Nuclear Medicine 43rd Annual Meeting, Denver, Co., June 3).

The present invention also provides a metal chelate based on a monothiourea (MTU) structure and having the general formula (II)

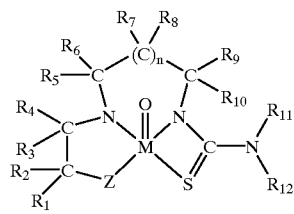

wherein n=0 or $R_1$–$R_{12}$ are individually selected from the group consisting of hydrogen, a straight or branched, unsubstituted or substituted alkyl having C=1–4, and ACOOH wherein A is a straight or branched, unsubstituted or substituted alkyl group having C=0–4;

$R_1$ together with $R_2$, $R_3$ together with $R_4$, and R. together with $R_6$ may form an oxygen atom;

$R_{11}$ and $R_{12}$ may alternatively be selected individually from the group consisting of

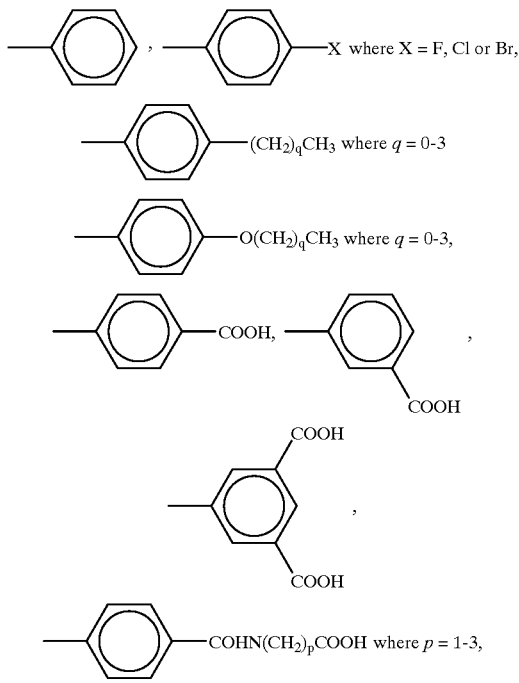

—$(CH)_p$COOH where p=0 or 2; and
—$CH_2CONH(CH_2)_p$COOH where p=1–3;

Z is selected from the group consisting of S and $N(CH_2)_p$COOH where p=1–3; and M is selected from the group consisting of Tc, Re, Cd, Pb, Zn, Hg, Ag, Au, Ga, Pt, Pd, Rh, Cr and V;

with the provision that (a) at least one of $R_1$–$R_{10}$ is ACOOH or, together with one other R group, forms an oxygen atom; and/or (b) only one of $R_1$, $R_2$, $R_3$ or $R_4$ and $R_5$, $R_6$, $R_7$ or $R_8$ and $R_7$, $R_8$, $R_9$ or $R_{10}$ is a straight or branched, unsubstituted or substituted alkyl of $C_3$ or $C_4$, a hydroxy-alkyl, or is an ACOOH wherein A is a straight or branched, unsubstituted or substituted alkyl group having C=0–4.

This group of metal chelates is exemplified in particular by structural formulae of $^{99m}$Tc chelates based on an acetamidethiourea structure as illustrated in FIG. 2, i.e., thioacetamidethiourea-phenyl (TATU-Ph), thioacetamidethiourea-phenylmethoxy (TATU-PhOCH.), thioacetamidethiourea-phenylchloro (TATU-PhCl), thioacetamidethiourea-methyl (TATU-CH$_3$), thioacetamidethiourea-dimethyl (TATU-(CH$_3$)$_2$), thioacetamidethiourea-para-phenylCOOH (TATU-pPhCOOH), thioacetamidethiourea-meta-phenylCOOH (TATU-mPhCOOH), thioacetamidethiourea-meta-phenyl (COOH)$_2$ (TATU-mPh(COOH)$_2$), thioacetamidethiourea-ethylCOOH (TATU-EtCOOH), thioacetamidethiourea-carboxylic acid (TATU-COOH), thioacetamidethiourea-hippuric acid (TATU-hippuric acid), thioacetamidethiourea-glycylglycine (TATU-glygly), dimethylthioacetamidethiourea-ethylCOOH ((Me)$_2$-TATU-EtCOOH), and dimethylthioacetamidethiourea-hippuric acid ((Me)$_2$-TATU-hippuric acid, dimethylthioacetamidepropylthiourea-ethylCOOH ((Me)$_2$-TAPTU-EtCOOH), dimethylthioacetamidepropylthiourea-hippuric acid ((Me)$_2$TAPTU-hippuric acid) and glycylglycyl-β-propionyl-thiourea (TPG$_2$). It was observed that the dimethyl-thioacetamidepropylthiourea-EtCOOH (dimethyl-TAPTU-EtCOOH) compound appeared to be more stable than the corresponding thioacetamidethiourea derivative.

Metal chelates based on an monothiourea (MTU) structure are suitable as pharmaceutical agents for renal imaging and examination of renal function. In particular, it was observed that the thioacetamidethiourea-EtCOOH (TATU-EtCOOH) metal chelate with technetium-99m exhibited superior renal clearance in rats when compared to a corresponding metal chelate with MAG3. Thioacetamidethiourea-pPhCOOH (TATU-pPhCOOH) was cleared at a moderate rate by the kidneys in rat.

Additionally, the present invention provides a metal chelate based on a dithiourea (DTU) structure and having the general formula (III)

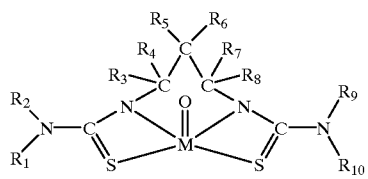

wherein $R_1$–$R_{10}$ are individually selected from the group consisting of hydrogen, a straight or branched, unsubstituted or substituted alkyl having C=1–4, and ACOOH wherein A is a straight or branched, unsubstituted or substituted alkyl group having C=0–4;

$R_1$, $R_2$, $R_9$ and $R_{10}$ may alternatively be selected individually from the group consisting of

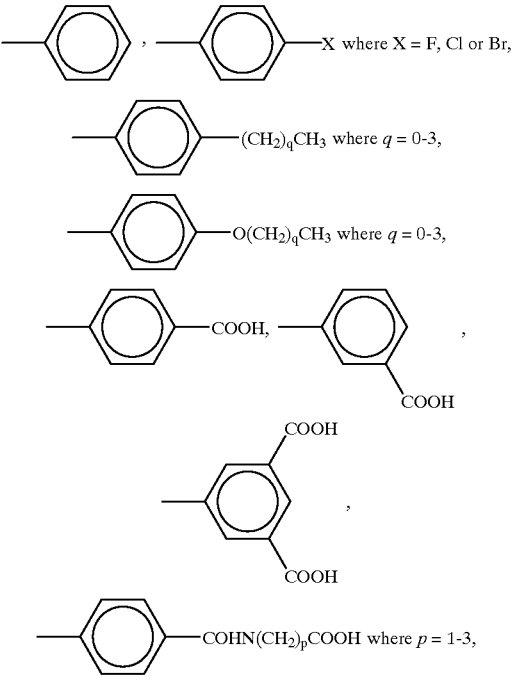

—$(CH_2)_p$COOH where p=0 or 2, and
—$CH_2CONH(CH_2)_p$COOH where p=1–3; and

M is selected from the group consisting of Tc, Re, Cd, Pb, Zn, Hg, Ag, Au, Ga, Pt, Pd, Rh, Cr and V;

with the provision that only one of $R_1$ and $R_2$, and $R_3$, $R_4$, $R_5$, or $R_6$, and $R_5$, $R_6$, $R_7$ or $R_8$, and $R_9$ or $R_{10}$ is a straight or branched, unsubstituted or substituted alkyl of C3 or $C_4$, or is an ACOOH wherein A is a straight or branched, unsubstituted or substituted alkyl group having C=0–4.

This dithiourea-based group of metal chelates is exemplified in particular by structural formulae of $^{99m}$Tc or Re chelates as illustrated in FIG. 3, i.e., dithiourea-phenyl (DTU-Ph), dithiourea-phenylmethoxy (DTU-PhOCH$_3$), dithiourea-methyl (DTU-CH$_3$), dithiourea-phenylCOOH (DTU-PhCOOH), dithiourea-ethylCOOH (DTU-EtCOOH), dithiourea-carboxylic acid (DTU-COOH), ethyl-dithiourea-phenyl (Et-DTU-Ph), dimethyl-dithiourea-phenylmethoxy ((Me)$_2$-DTU-PhOCH$_3$), carboxyl-dithiourea-phenyl (COOH-DTU-Ph), and methyl-dithiourea-ethylCOOH (Me-DTU-EtCOOH).

In addition to each of the compounds illustrated above, the present invention comprises the water-soluble salts thereof and includes, but is not limited to, the replacement of a hydrogen with suitable, pharmaceutically acceptable, positively charged ions such as Na+, K+, Li+, $Ca^{2+}$ or $Sr^{2+}$ and the like. Pharmaceutically acceptable salts may be salts with ions of alkali metals, alkaline earth metals, or suitable transition metals.

The novel metal chelates of the present invention are used in renal imaging procedures by administration thereof, preferably via intravenous injection, into a patient, human or animal. Images of the patient's kidneys are recorded by means of gamma scintillation cameras. The dosage of the metal chelate required for imaging is controlled in part by the character of the radionuclide making up the metal chelate. For example, it is possible to administer dosages of as much as 30,000 microcures of $^{99m}$Tc. The ability to use such a substantial dosage is extremely beneficial in conducting dynamic tests of renal function in that shorter periods of exposure to the radionuclide are possible with higher dosages.

It has been found that the novel metal chelates of the invention, for example, the $^{99m}$Tc chelates, are actively secreted into the kidney tubules, thereby providing significantly high extraction efficiencies.

From an examination of the structures set forth in FIGS. 1, 2 and 3, it will be appreciated that the novel compounds need not exist in stereoisomeric forms that might lessen the practical applications of these compounds. Diasteriomeric forms of the compounds may be precluded upon a proper choice of substituent groups during synthesis of the compounds.

The present invention is also directed to organic molecules (ligands) which are capable of tightly chelating with a nuclide to form a foregoing metal chelate of the invention. A ligand suitable for the preparation of a metal chelate of general formula (I) has a cysteinylethylene-based chemical structure defined by general formula (IV)

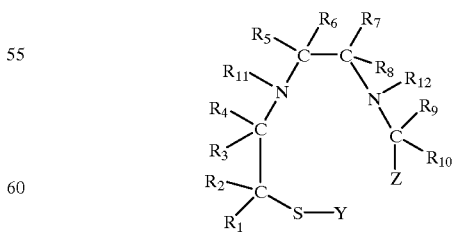

wherein $R_1$–$R_{12}$ are individually selected from the group consisting of hydrogen, a straight or branched, unsubstituted or substituted alkyl having C=1–4, a hydroxy-alkyl, and ACOOH wherein A is a straight or branched, unsubstituted or substituted alkyl group having C=0–4;

$R_3$ together with $R_4$, $R_5$ together with $R_6$, $R_7$ together with $R_8$, and $R_9$ together with $R_{10}$ may form an oxygen atom;

Z is selected from the group consisting of

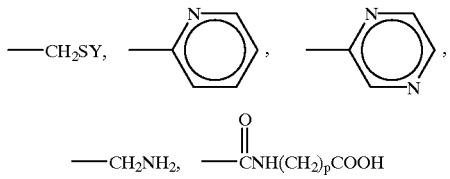

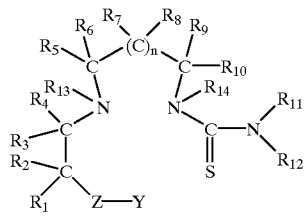

where p=1–3, and

—$CH_2NH(CH_2)_p$COOH where p=1–3; and

Y is a hydrogen atom or a suitable protecting group;

with the provision that (a) at least one of $R_1$–$R_{10}$ is ACOOH or, together with one other R group, forms an oxygen atom; and/or (b) only one of $R_1$, $R_2$, $R_3$ or $R_4$ and $R_5$, $R_6$, $R_7$ or $R_8$ and $R_9$ or $R_{10}$ is a straight or branched, unsubstituted or substituted alkyl of $C_3$ or $C_4$, a hydroxy-alkyl, or is an ACOOH wherein A is a straight or branched, unsubstituted or substituted alkyl group having C=0–4.

A new class of $N_2S_2$ ligands (the monothiourea (MTU) ligands), based on thiol, amide and thiourea donor groups, is provided by the present invention for the preparation of a metal chelate of general formula (II). Such a ligand having an MTU-based structure is defined by the general formula (V).

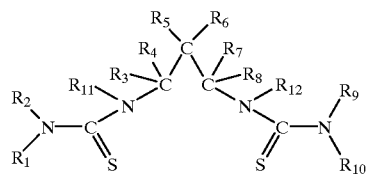

wherein n=0 or 1, $R_1$–$R_{14}$ are individually selected from the group consisting of hydrogen, an alkyl having C=1–4 a hydroxy-alkyl, and ACOOH wherein A is a straight or branched, unsubstituted or substituted alkyl group having C=0–4;

$R_1$ together with $R_2$, $R_3$ together with $R_4$, and $R_5$ together with $R_6$ may form an oxygen atom;

$R_{11}$ and $R_{12}$ may alternatively be selected individually from the group consisting of

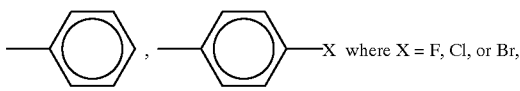

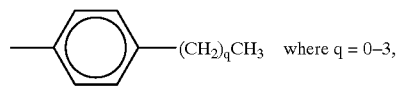

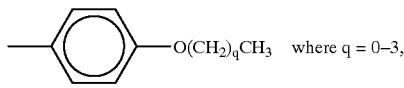

-continued

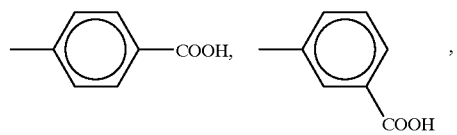

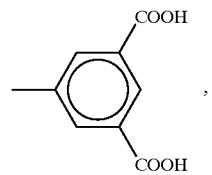

—$(CH_2)_p$COOH where p=0 or 2, and

—$CH_2CONH(CH_2)_p$COOH where p=1–3;

Z is selected from a group consisting of S and $N(CH_2)_p$COOH where p=1–3; and

Y is a hydrogen or a suitable protecting group;

with the provision that (a) at least one of $R_1$–$R_{10}$ is ACOOH or, together with one other R group, forms an oxygen atom; and/or (b) only one of $R_1$, $R_2$, $R_3$ or $R_4$ and $R_5$, $R_6$, $R_7$, or $R_8$ and $R_7$, $R_8$, $R_9$ or $R_{10}$ is a straight or branched, unsubstituted or substituted alkyl of $C_3$ or $C_4$, a hydroxy-alkyl, or is an ACOOH wherein A is a straight or branched, unsubstituted or substituted alkyl group having C=0–4.

In addition, a new class of $N_2S_2$ ligands is provided by the present invention for the preparation of metal chelates of general formula (III). Such a ligand is based on a dithiourea (DTU) structure and is defined by the general formula (VI)

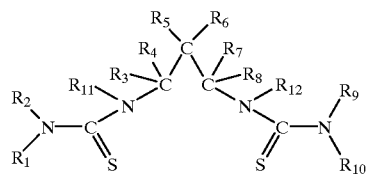

wherein $R_1$–$R_{12}$ are individually selected from the group consisting of hydrogen, a straight or branched, unsubstituted or substituted alkyl having C=1–4, a hydroxy-alkyl, and ACOOH wherein A is a straight or branched, unsubstituted or substituted alkyl group having C=0–4;

$R_1$, $R_2$, $R_9$ and $R_{10}$ may alternatively be selected individually from the group consisting of

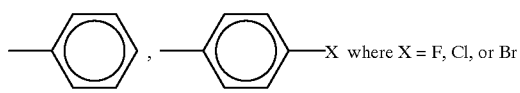

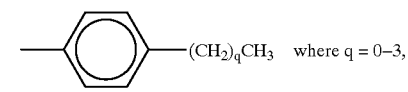

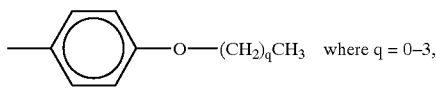

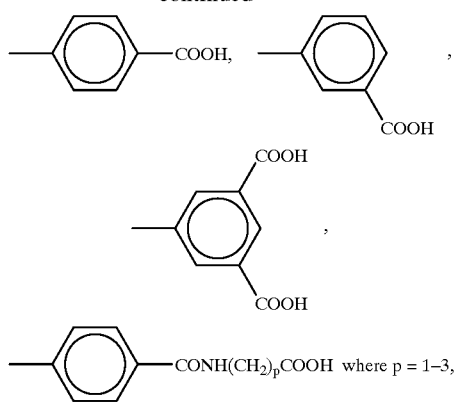

—CONH(CH$_2$)$_p$COOH where p = 1–3,

—(CH$_2$)$_p$COOH where p=0 or 2, and
—CH$_2$CONH(CH$_2$)$_p$COOH where p=1–3;
with the provision that
only one of R$_1$ and R$_2$, and R$_3$, R$_4$, R$_5$, or R$_6$, and R$_5$, R$_6$, R$_7$ or R$_8$, and R$_9$ or R$_{10}$ is a straight or branched, unsubstituted or substituted alkyl of C$_3$ or C$_4$ a hydroxy-alkyl, or is an ACOOH wherein A is a straight or branched, unsubstituted or substituted alkyl group having C=0–4.

Examples of suitable protective groups Y for ligands having the general formulas IV, V and VI include, but are not limited by, acetyl, trifluoroacetyl, hydroxyacetyl, carboxyacetyl, acetamidomethyl, benzoyl, benzyl, benzoylaminomethyl, triphenylmethyl and the like.

Some of the new compounds of this invention may occur as optical isomers, which may readily be separated by art known methods used for this purpose. The biological properties of different diastereomeric compounds may differ. The yield of a desired diastereomer may be influenced by adjusting the reaction conditions, e.g., the pH, as taught in the art.

The radioactive properties of $^{99m}$Tc make it ideal for use in nuclear medicine and other biological purposes. Technetium-99m is currently considered to be the most desirable radioactive label, primarily because $^{99m}$Tc emits a relatively low energy (140 KeV) radiation, because $^{99m}$Tc has a half-life of only about six hours, and also because $^{99m}$Tc does not emit beta particles during its decay process. Dosages of as much as 30,000 microcuries, and preferably between 0.1 and 30 mCi per 70 kg of body weight, of $^{99m}$Tc may be administered without danger to the patient and, in view of this permissible high dosage, only a relatively short exposure period is required, for example, in renal imaging.

In view of the short half-life of $^{99m}$Tc, it is appreciated that the stability of a $^{99m}$Tc-chelate to be used for renal examination is of great importance, for there must be sufficient time to complete a renal examination without the possibility of contamination due to formation of disintegration products. Thus, $^{99m}$Tc imaging compounds must be prepared immediately prior to conducting a kidney function diagnostic procedure.

An important feature of the present invention is the ability to package in a kit form the chemical reagents necessary for the easy preparation of a metal chelate, e.g., $^{99m}$Tc-chelate, immediately prior to use as a radiopharmaceutical. By means of a kit, the labeling reaction of a ligand with a radionuclide may be carried out just prior to use in a clinical laboratory setting that has access to a molybdenum-technetium generator, from which a desired quantity of $^{99m}$Tc can be easily obtained as a pertechnetate solution.

The kit provided by the present invention for formation of a radiopharmaceutical chelate suitable for renal examination comprises a ligand having a structure according to one of the general formulas (IV), (V) or (VI) and a reducing agent. A stabilizing agent and/or a chelating agent, as well as instructions for use of the reagents in the kit, may be included within the kit.

According to the invention, a metal chelate, e.g., a $^{99m}$Tc-chelate, is prepared from a kit by interacting under reducing conditions the reactants of the kit, i.e., a ligand and reducing agent, with a freshly prepared $^{99m}$Tc pertechnetate solution eluted from a molybdenum-technetium generator just prior to use. The $^{99m}$Tc may be present in the form of a salt or as technetium bound to a relatively weak chelator, in which case the desired $^{99m}$Tc chelate is formed by ligand exchange. Examples of relatively weak chelating agents known to be particularly suitable to easily obtain a desired ligand exchange are, for example, carboxylic acids such as citric acid, tartaric acid, ascorbic acid, glucoheptonic acid, and derivatives thereof, although polycarboxylic acids, hydroxycarboxylic acids and phosphorus compounds can also be used.

Suitable reducing conditions to keep the $^{99m}$Tc pertechnetate reduced can be provided by, for example, dithionite, formamidine sulfinic acid or metallic reducing agents such as Fe(II), Cu(I), Ti(III) or Sb(III) and, preferably, Sn(II).

The reactants of the kit may be present in liquid form, for example, as a saline or buffer solution. However, it is preferred that the reactants be in a dry form, e.g., a lyophilized condition. The reactants may be stabilized by the presence of a suitable stabilizing agent such as ascorbic acid, gentisic acid, sugar, e.g., glucose, lactose, mannitol, inositol, and the like.

It will be apparent to those of ordinary skill in the art that alternative methods, reagents, procedure and techniques other than those specifically detailed herein can be employed or readily adapted to practice the detection methods of this invention. Such alternative methods, reagents, procedures and techniques are within the spirit and scope of this invention.

All publications, references, patent applications and patents cited herein are incorporated by reference in the same extent as if each individual publication, patent application or patent were specifically and individually indicated to be incorporated by reference.

The methods of this invention are further illustrated in the following non-limiting Examples. All abbreviations used herein are standard abbreviations in the art. Specific procedures not described in detail in the Examples are well-known in the art.

EXAMPLES

Example 1

Synthesis of Cysteinylethylene (CE)-Based Ligands

Substantial progress has been made in protection-deprotection chemistry of cysteine allowing cysteine to be successfully used in peptide synthesis [Nokihara et al., J. Org. Chem. (1978) 43: 4893; Kemp et al., J. Org. Chem. (1989) 54: 3640; Theradgill et al., J. Org. Chem. (1989) 54: 2940]. Thus, cysteine derivatives have been attractive as potential sources of pharmaceuticals. In particular, $^{99m}$Tc L,L-ethylenedicysteine diethyl ester ($^{99m}$Tc LL-ECD) is reported to be a good brain perfusion agent [Cheesman et al., J. Nucl. Med. (1988) 29: 788; Vallabhajosula et al., J. Nucl. Med. (1988) 29: 921] and its most polar metabolite ($^{99m}$Tc LL-EC) is excreted rapidly and efficiently by the kidneys [Verbruggen et al, In: *Technetium and Rhenium in Chemistry and Nuclear Medicine* 3 (Nicolini, M., Bandoli, G., Mazzi, U., eds.) New York: Cortina International and Raven Press (1990) 445–452]. These EC ligands have two dangling carboxyl groups; conceivably, a simpler agent would have only one carboxyl group and thus EC-based compounds were synthesized with only one cysteine.

Figure 4:
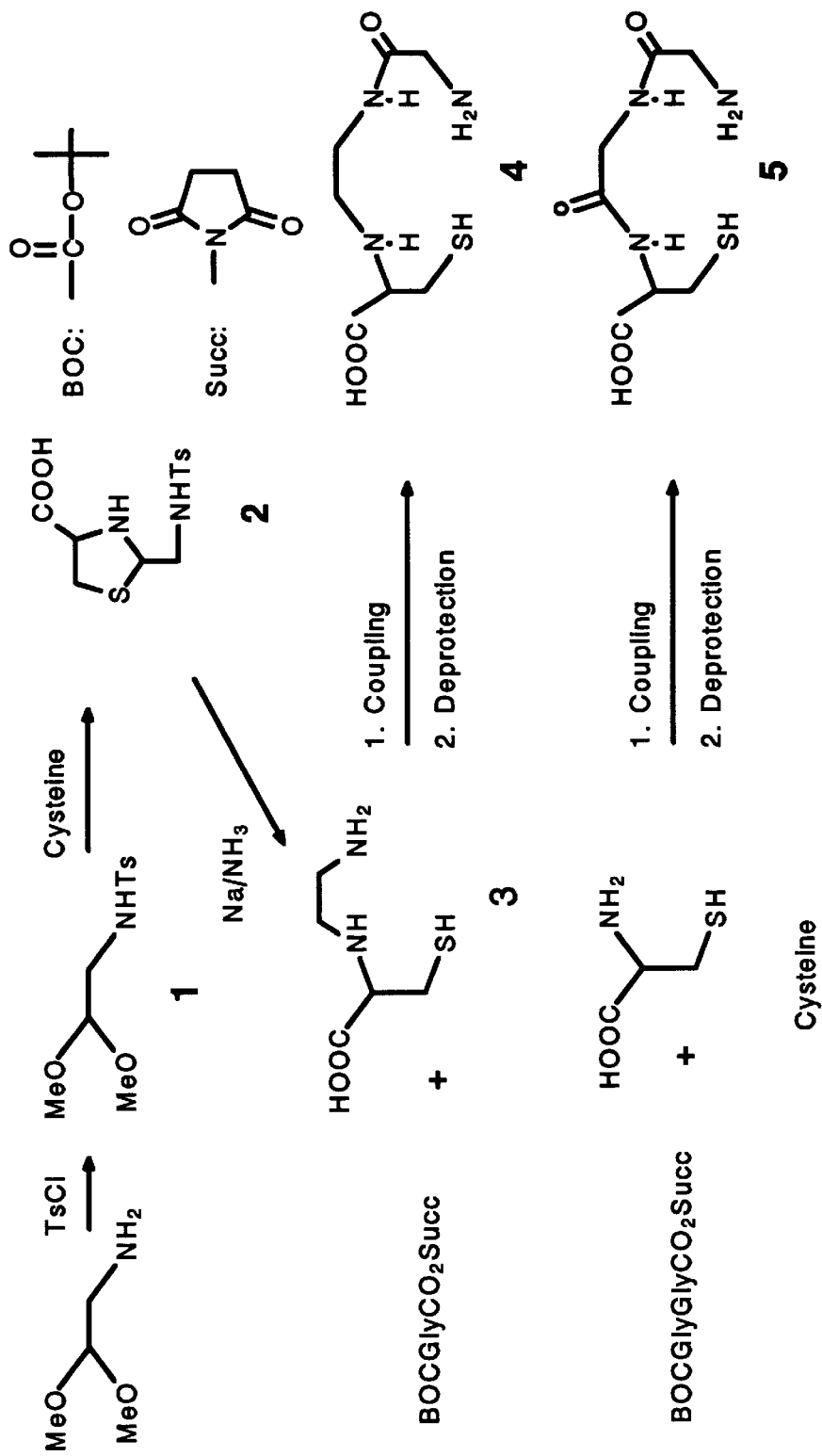
FIG. 4 presents Scheme 1, illustrating synthetic pathways for the synthesis of one-cysteine ligands.

1.1. Synthesis of $N_3S$ Ligands 1.1.A. Amine-Diamide-Thiol or Amide-Diamine-Thiol Syntheses for one-cysteine ligands are presented in Scheme 1 (FIG. 4). The ligands 4 (CEG) and 5 (cysteinylglycylglycine CGG) were prepared by methods common to peptide synthesis, namely the use of activated esters and coupling reagents [Bodansky et al., *Peptide Synthesis*, New York: Wiley (1976)] and of the BOC (tert-butoxycarbonyl) protecting group [Green, *Protective Groups in Organic Synthesis*, New York: Wiley (1981)].

Intermediate 3 was obtained by reduction of thiazolidine 2 derived from D- or L-cysteine with sodium in liquid ammonia. Then 3 was coupled with an N-hydroxysuccinimide activated ester of BOC-glycine to form the BOC-protected ligand. Hydrolytic removal of the BOC group [Green, *Protective Groups in Organic Synthesis*, New York: Wiley (1981)] furnished the amide-diamine-thiol ligand 4 (CEG), which was ready for labeling with $^{99m}$Tc. Similar condensation of D- or L-cysteine with the N-hydroxy-succinimide activated ester of BOC-glycylglycine produced the amine-diamide-thiol ligand 5 (CGG). All amino acids and their BOC-protected forms are commercially available.

1.1.B. Introduction of Nitrogen Heterocyclic Atom

Figure 5:
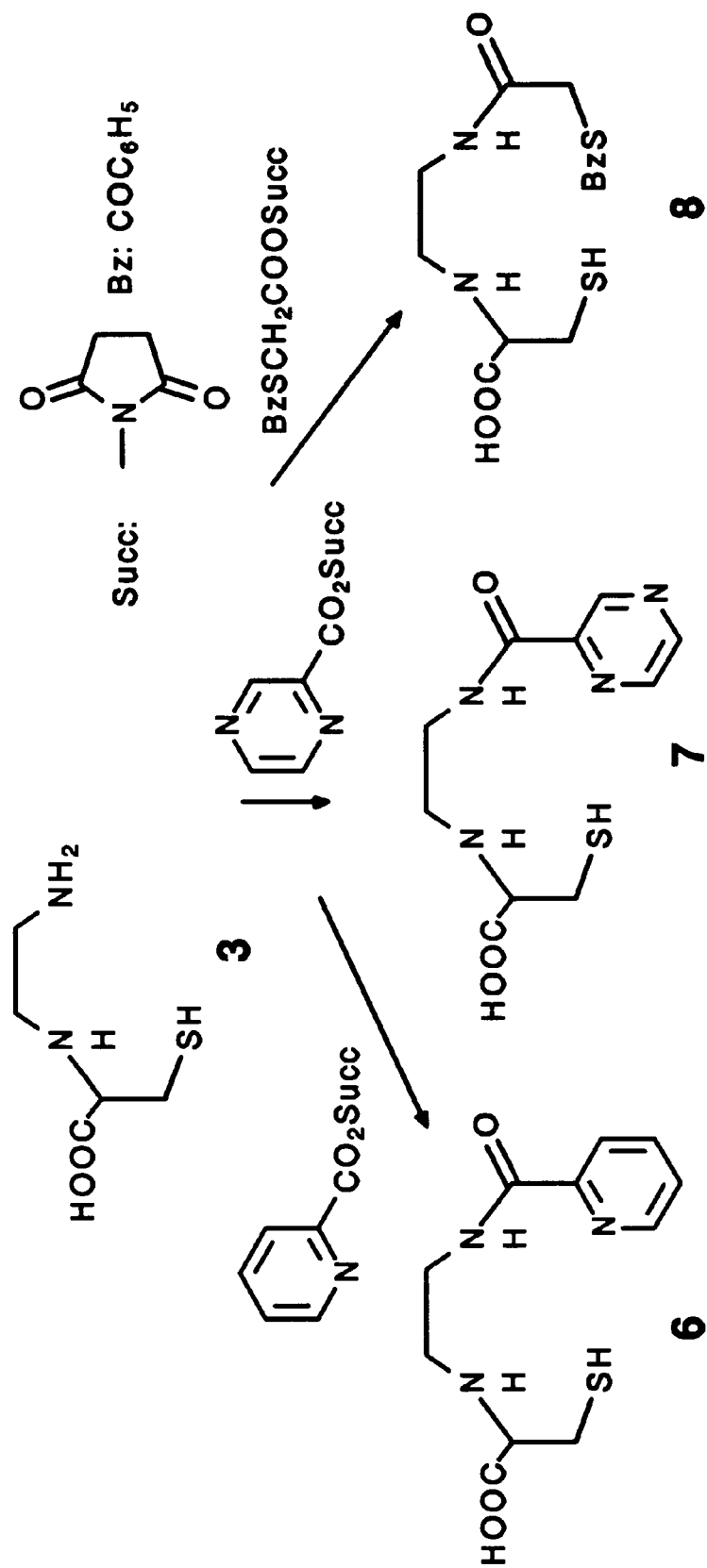
FIG. 5 presents Scheme 2, illustrating synthetic routes for the synthesis of $N_3S$ amide-amine-N-heterocyclic-thio ligands.

The synthesis takes advantage of the versatility of nitrogen heterocyclic systems and their α-carboxyl derivatives. The synthetic route for preparation of $N_3S$ amide-amine-N-heterocyclic-thiol ligands from intermediate 3 is outlined in Scheme 2 (FIG. 5). Condensation of N-hydroxysuccinimide activated ester of α-carboxyl nitrogen heterocyclic compounds such as picolinic acid or 2-pyrazinecarboxylic acid with 3 led to ligands 6 and 7 (L-CEPIC, D-CEPIC, CEPZ), respectively.

1.1C Synthesis of Cysteinylacetylglycylglycine ($CAG_2$)

Figure 6:
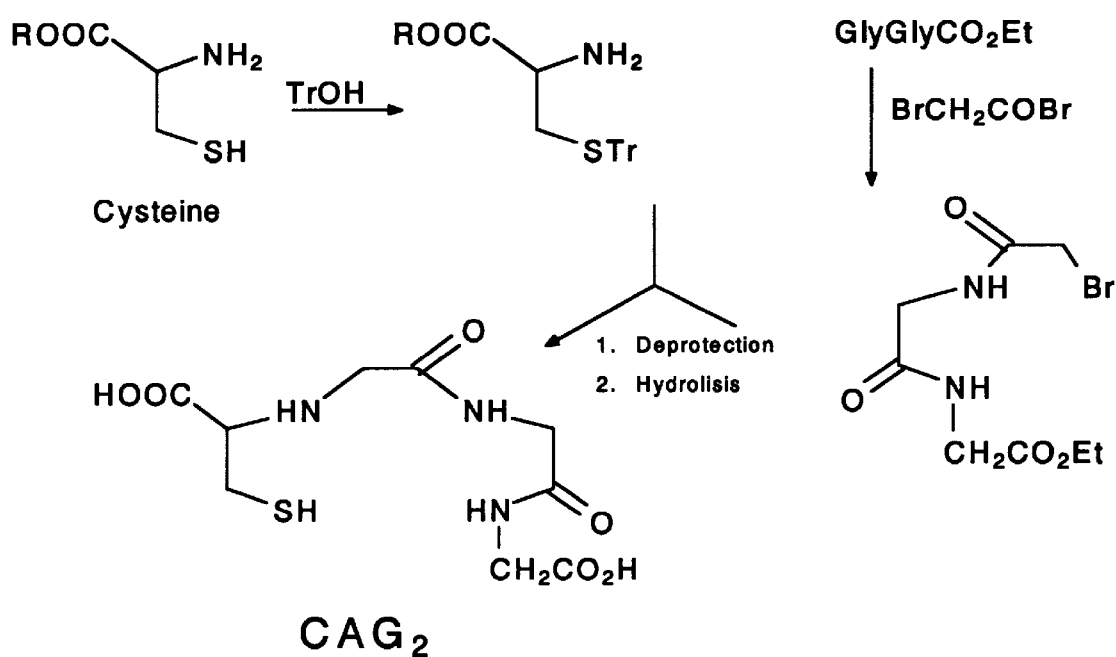
FIG. 6 presents schematically the synthesis of cysteinylacetylglycylglycine (CAG$_2$).

An $N_3S$ ligand system was also synthesized to combine features of EC, which has favorable protein binding characteristics, and MAG3, which has a favorably high extraction rate. The procedure is presented schematically in FIG. 6. $CAG_2$ combined chemical features of EC (cysteine) and MAG3 (terminal glycine). Glycylglycine ethyl ester was treated with bromoacetyl bromide in anhydrous DMF in the presence of dry sodium carbonate to give bromo derivative. The obtained bromide was reacted with one equivalent of S-trityl protected cysteine ethyl ester. Following deprotection of sulfur and hydrolysis of the ester, $CAG_2$ was obtained.

1.2. Synthesis of $N_2S_2$ Ligands

Cysteinyl ethylene mercaptoacetamide (CEMA)

A new ligand system, cysteinyl ethylene mercaptoacetamide (CEMA), was synthesized to combine structural features of both CE and MAG3. Two isomers were prepared with either L- or D-cysteine. Intermediate 3 was coupled with succinimidyl-S-benzoylthioglycolate to form ligands 8 (L-CEMA and D-CEMA) (Scheme 2 in FIG. 5). Biodistribution studies in rats showed that the $^{99m}$Tc complexes with both D-CEMA and L-CEMA are efficiently extracted by the kidneys (~80% of the injected dose was found in the kidneys and bladder 30 minutes post injection).

Example 2

Synthesis of Monothiourea (MTU)-based Ligands

Synthesis of $N_2S_2$ Ligands 2.1. Monothiourea (MTU)

Figure 7:
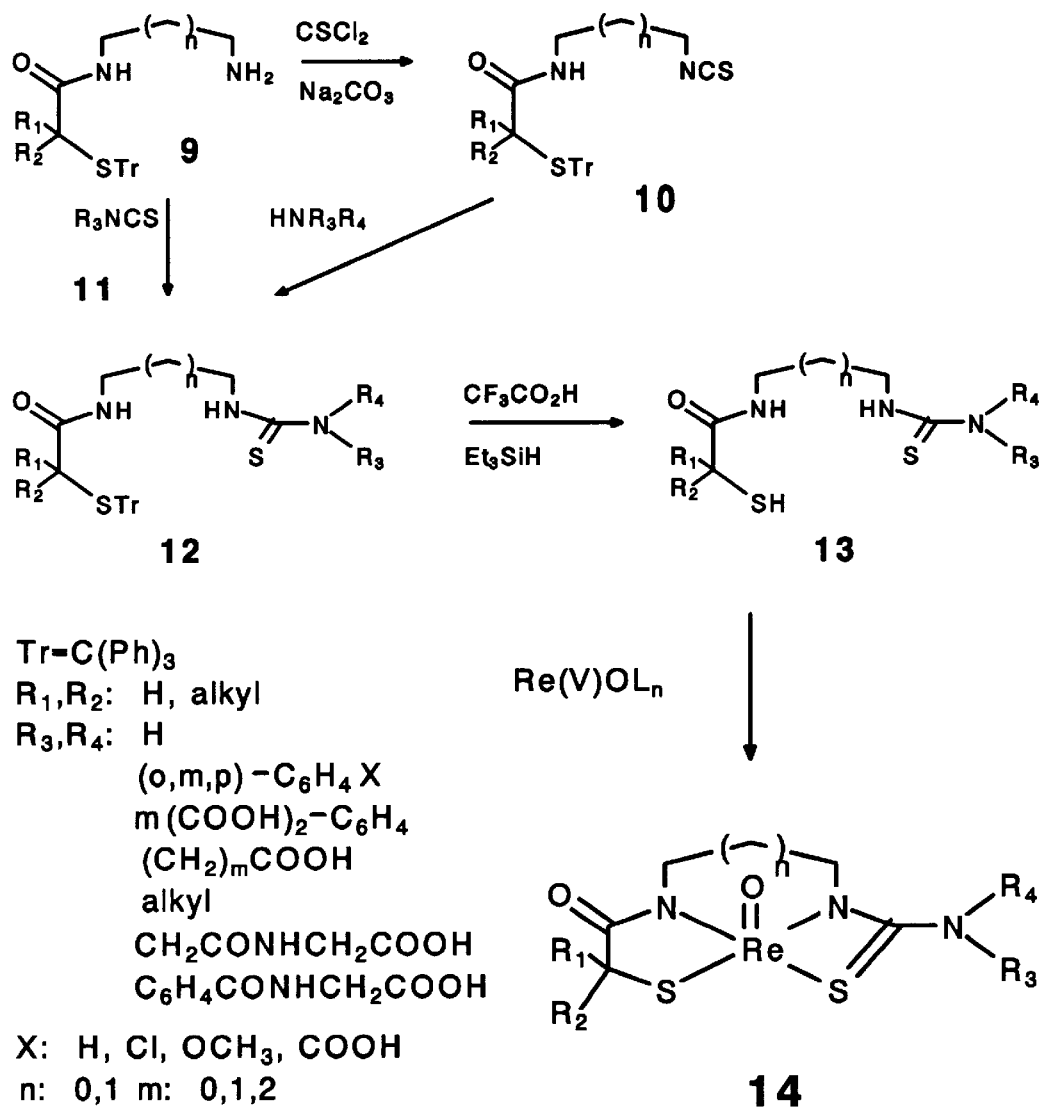
FIG. 7 presents Scheme 3, illustrating the synthesis of monothiourea (MTU) ligands.

The proposed synthesis for this class of ligand is represented in Scheme 3 (FIG. 7).

N-(2-Aminoethyl)-2-((triphenylmethyl)thio)acetamide (9) is a known ligand precursor for the synthesis of the diamide-thiol-thioether ($N_2S_2$) [Bryson, N. et al., Inorg. Chem. (1988) 27: 2154] and diamide-thiol-pyridine ($N_3S$) [Bryson, N. et al., lnorg. Chem (1990) 29: 2948] $^{99m}$Tc(V)O complexes which were designed in the development of $^{99m}$Tc radiopharmaceuticals. The importance of this precursor lies in the presence of the three potential donor sites, the sulfur atom and two nitrogen atoms. The terminal primary amine can be used to extend the ligand by methods common to peptide synthesis, namely the use of activated esters and coupling reagents for the formation of amide bonds. [Bodansky et al., *Peptide Synthesis*. New York: Wiley (1976)]

Primary amines also rapidly react with the isothiocyanate group to form a stable thiourea linkage. This approach was used for the straightforward preparation of a new series of thiol-amide-thiourea $N_2S_2$ (TATU) ligands according to the route shown in Scheme 3 (FIG. 7). This is a versatile approach for the synthesis of thiourea chelate ligands since a variety of isothiocyanate agents are commercially available and many amine precursors can be used to construct polydentate ligands. The reactions of amine 9 ($R_1$, $R_2$=H, n=0) with appropriate isothiocyanates 11 (Scheme 3) were performed in ethanol solution at room temperature and gave thiourea ligands 12 in Very good yield (TATU-Ph, TATU-PhOCH$_3$, TATU-PhCl, TATU-CH$_3$). We modified the TATU ligands by introducing a carboxylate moiety into the ligand system by reaction of 9 with isothiocyanates 11 derived from alkyl or aromatic amines containing an ester group, i.e., ethyl 3-isothiocyanatobutyrate (TATU-EtCOOH), ethoxycarbonyl isothiocyanate (TATU-COOH), 3-, or 4-ethoxycarbonylphenyl isothiocyanate (TATU-pPhCOOH, TATU-mPhCOOH, TATU-mPh(COOH)$_2$). By the reaction of precursor 9 ($R_1$, $R_2$=alkyl, n=1) with isothiocyanate 11, the new group of thioacetamideproyl-thiourea (TAPTU) ligand was also synthesized, e.g., (Me)$_2$-TAPTU-EtCOOH and (Me)$_2$-TAPTU-hippuric acid. The ethyl ester group has been chosen to increase the solubility of the isothiocyanates in organic solvents and facilitate purification of the products (12), which will be less polar than the carboxylate derivatives. The ethyl esters are readily cleaved to free carboxylates under standard $^{99m}$Tc labeling conditions.

The variety of MTU ligands that may be prepared can be greatly increased by conversion of the primary amine to isothiocyanate and then treatment with an amine. A successful example of this approach is also given in Scheme 3. 9 was treated with thiophosgene in the presence of sodium carbonate to furnish the isothiocyanate derivative 10 in moderate yield (62%). Compound 10 gave a strong infrared adsorption at 2100 cm$^{-1}$ which is characteristic for the isothiocyanate function. The treatment of 10 with a methanol solution of secondary amine gave the expected N,N-dialkyl thiourea derivative 12 (TATU-(Me)$_2$). This alternative approach was used in the synthesis of TATU-GlyGly or TATU-hippuric acid-type ligand intermediates containing a peptide or 4-aminohippurate in the side chain.

In all reactions, S-protected thiourea derivatives 12 were the major product and purification of ligands 12 was simple. Column chromatography to remove the polymeric materials and then crystallization from ethanol were sufficient to obtain compounds of high purity. The spectroscopic and analytical data obtained for these protected ligands were consistent with the structures shown. The simplicity and efficiency of the preparation of these compounds indicate that these $N_2S_2$ thiourea chelates represent a new class of readily prepared, versatile ligands.

The free thiol ligands were cleanly isolated by dissolving the S-triphenylmethyl (STr) protected derivatives 12 in trifluoroacetic acid, titrating the deep yellow $Tr^+$ cation with triethylsilane until the solution was colorless, extracting with hexane (to remove TrH), and evaporating the solvent. The proposed structures of the resulting compounds 13 in Scheme 3 were consistent with analytical and $^1H$ NMR spectral data.

Re(V)O complexes of MTU ligands 13 were prepared by ligand exchange in basic methanol solution with $ReOCl_3$ $(Me_2S)(OPPh_3)$ or $ReO_2I(PPh_3)_2$ (Scheme 3) to give 14. These precursors can be used interchangeably with the MTU ligands with very good results. Direct reduction with $SnCl_2$ of $TcO_4^-$ in the presence of MTU ligands under basic conditions was effective but not for $ReO_4^-$, which is more difficult to reduce than $TcO_4^-$. [Rao et al., J. Am. Chem. Soc. (1990) 112: 5798; Marzilli et al., Inorg. Chem. (1994) 33: 4850; Francesconi et al., Inorg. Chem. (1993) 32: 3114.] The complexes 14 were air-stable solids and were characterized by elemental analysis, FT IR, and $^1H$ NMR spectroscopy.

Figure 8:
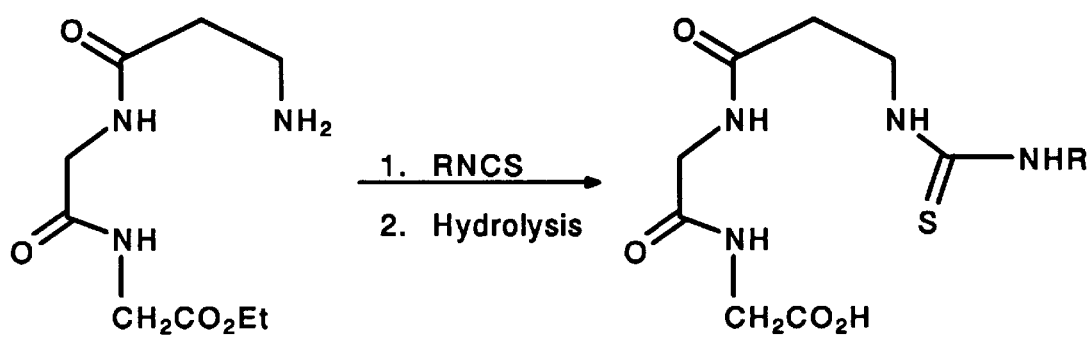
FIG. 8 presents schematically the synthesis of glycylglycyl-β-propionyl-thiourea (TPG$_2$).

New analogs of the promising MTU type of ligand, derived from beta alanine and linked via thiourea function, were synthesized (schematically presented in FIG. 8). Beta-alanylglycylglycine ethyl ester reacted with isothiocyanates to give, after hydrolysis of the ester, ligands with one or two carboxyl groups. Synthesis of the glycylglycyl-β-propionyl-thiourea ($TPG_2$) ligands does not require protection and deprotection of the sulfur atom.

2.2. Dithiourea (DTU)

Scheme 4 (FIG. 9) illustrates the synthetic route utilized in the one step preparation of the dithiourea ligands (DTU) 16 and their rhenium complexes 17.

A variety of alkyl and aryl diamines (15) are commercially available and are good starting materials for the synthesis of dithiourea chelates. Reaction of amine derivatives with isothiocyanates leading to the formation of a thiourea linkage is well known [Drobnica et al., "The Chemistry of the -NCS Group." In: Patai, S., ed. *The Chemistry of cyanates and Their Thio Derivatives*, Part 2. Chichester: Wiley (1977) 1003–1221]. Furthermore, isothiocyanates are stable in water and react rapidly with primary amines in aqueous environments at pH 8–9. This is very important because many polar carboxy-substituted isothiocyanates are soluble only in aqueous solutions unless they are derivatized. Depending on the molar ratio of the starting materials, several possible products are expected.

2.2.A. Symmetrical Dithiourea (DTU) Ligands

In the 2:1 (isothiocyanate:amine) molar ratio symmetrical dithiourea (DTU) ligands were formed (DTU-Ph, DTU-$PhOCH_3$, DTU-$CH_3$). Unlike other $N_2S_2$ ligands, the DTU systems did not require prior deprotection of the sulfur atoms and were used directly in ligand exchange reactions. Previous studies involving $N_2S_2$ complexes of $^{99m}Tc$ have shown that efficient renal handling of these compounds is highly dependent on the position and the electronic and lipophilic nature of substituents on the chelate ring, and that the charge of these complexes may be a significant factor in determining the rate of renal excretion [Kasina et al., J. Med. Chem. (1986) 29: 1933]. Thus, using exactly the same procedure as we have reported for the synthesis of DTU ligands, and starting with carboxylate derivatives of isothiocyanate $(SCN-(CH2)_nCOOH, SCN-(Ar)-COOH)$, we developed a new group of dithiourea (DTU-COOH) ligands (DTU-PhCOOH, DTU-EtCOOH, DTU-COOH). $^{99m}Tc$ (DTU-COOH) complexes of the ligands containing two carboxyl moieties will be dianionic at physiological pH and have the potential of being renal radiopharmaceuticals.

Ethyl-dithiourea-phenyl (Et-DTU-Ph), dimethyl-dithiourea-phenylmethoxy (($Me)_2$-DTU-$PhOCH_3$), carboxy-dithiourea-phenyl (COOH-DTU-Ph) can be synthesized from corresponding amines using essentially the same procedures.

2.2.B. Non-Symmetrical DTU Ligands

Figure 9:
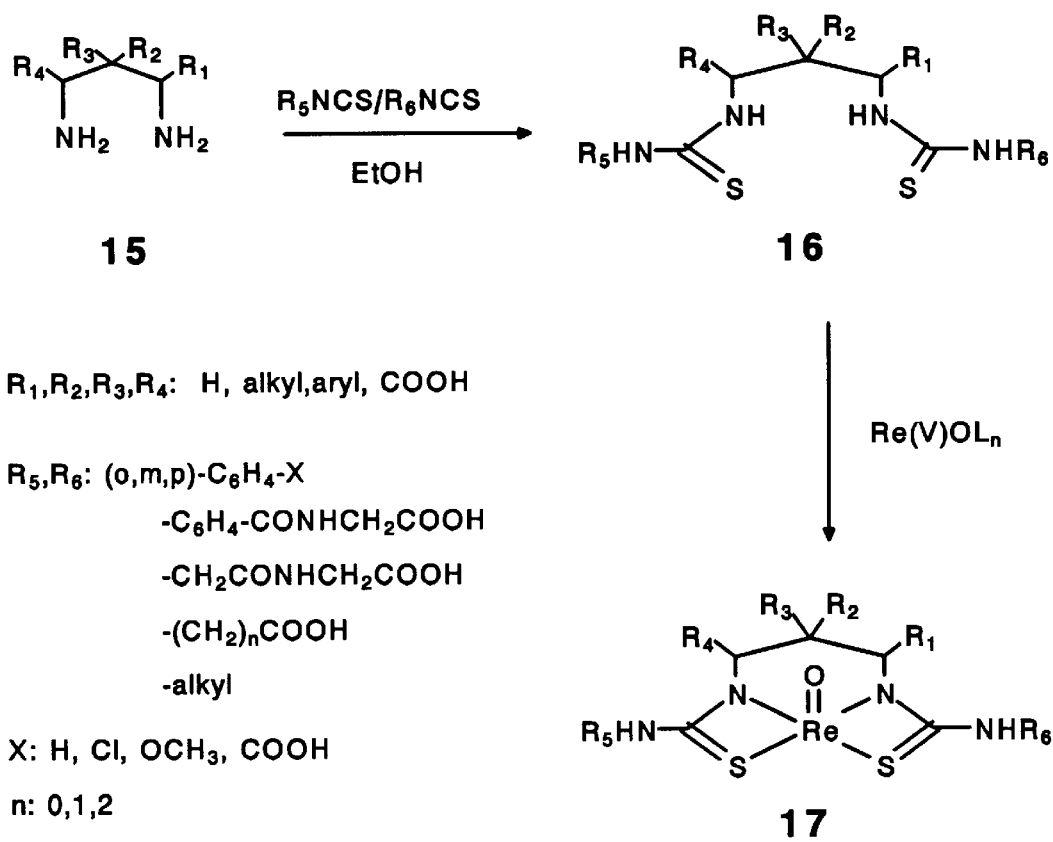
FIG. 9 presents Scheme 4, illustrating the synthetic route for a one-step preparation of a dithiourea ligand and its rhenium complex.

Non-symmetrical DTU ligands (e.g., Me-DTU-EtCOOH) containing two different terminal thiourea subunits were formed if a mixture of two different isothiocyanates (2:1 (R'NCS/R"NCS:diamine) molar ratio) was used (Scheme 4 in FIG. 9). The mixture of the three probable DTU ligands that arose (two symmetrical and one non-symmetrical) was separated by chromatography, especially with a Chromatotron. This approach did not only increase the number of ligands that could be prepared but allowed us to prepare monoanionic, mono-carboxylate agents.

Example 3

Synthesis of Thiol-Diamide-Amine (TDAA) Ligands

Synthesis of $N_3S$ Ligands

Figure 10:
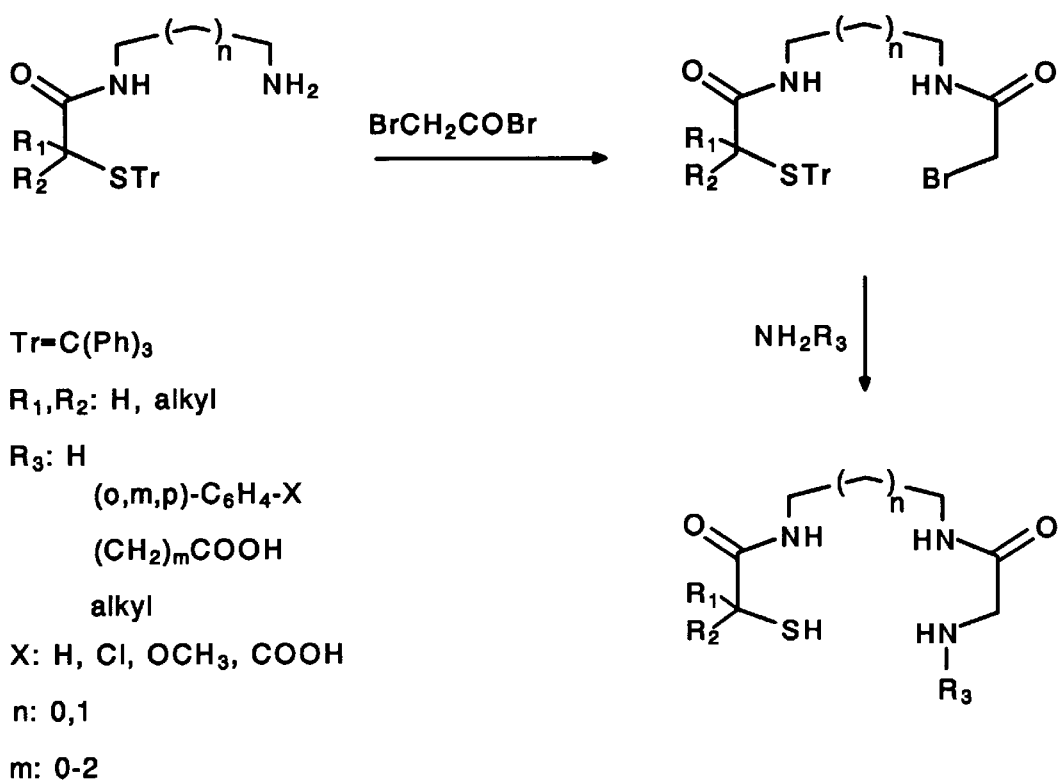
FIG. 10 presents Scheme 5, illustrating the pathway for synthesis of thiol-diamide-amine (TDAA) ligands.

The intermediate 9 was also a precursor for the preparation of thiol-diamide-amine (TDAA) ligands (Scheme 5 in FIG. 10).

N-Acylation of amine 9 with bromoacetyl bromine in the presence of triethylamine provided the primary bromine 18, which was then treated with one equivalent of amine to give the thiol-diamide-amine ligand (TDAA) (TDAA-$CH_3$, TDAA-EtCOOH).

Example 4

Preparation of Metal Chelates

A. General Procedure for Metal Chelates with Cysteinyl-ethylene (CE)-Based Ligands A cysteinylethylene (CE) ligand (1 mg) is dissolved in 1N NaOH (100 μl). To this solution is added a desired nuclide. The mixture is heated at 100° C. for 10 minutes, followed by addition of IN HCl (105 μl). The labeled EC complexes are isolated by reverse phase HPLC and analyzed to verify the nature of each product. This general procedure is applicable to nuclides including, but not limited to, Tc, Re, Cd, Pb, Zn, Hg, Ag, Au, Ga, Pt, Pd, Rh, Cr and V. Specific examples of the labeling procedure for particular CE ligands are presented in the following descriptions.

A.1. Preparation of $^{99m}Tc$ Labeled Ethylene Dicysteine (EC)

L,L-ethylenedicysteine, D,D-ethylenedicysteine and a mixture of D,D-, L,L- and D,L-ethylenedicysteine were prepared according to literature procedures [Ratner et al. (1937) J. Am. Chem. Soc. 59: 200–206; Blondeau et at. (1967) Can. J. Chem. 45: 49–52]. L-thiazolidine4- carboxylic acid and D-thiazolidine4-carboxylic acid prepared from optically pure L-cysteine and D-cysteine were reductively dimerized to give pure enantiomeric products. When the racemic cysteine was used to obtain the D,L-ethylenedicysteine ligand, the reaction yielded an isomeric mixture consisting of all three isomers.

Each ligand (1 mg) was dissolved in 1 N NaOH (100 µl). [$^{99m}$Tc]sodium pertechnetate in generator saline (0.25 ml) was added to the solution along with freshly prepared stannous chloride solution (4 mM, 0.02 M HCl, 100 µl). The mixtures were heated at 100° C. for 10 minutes followed by addition of 1 N HCl (105 µl). The $^{99m}$Tc-EC complexes were isolated by reverse phase HPLC on a Beckman Ultrasphere ODS 5 µm column (4.6×250 mm); flow rate 1 ml/min; mobile phase 0.05 M NaH$_2$PO$_4$, pH 4.3 or 0–10% EtOH gradient, 0.01 M NaH$_2$PO$_4$, pH 3.0 (1 min. gradient with $^{99m}$Tc DD and LL-EC and a 10 minute gradient for the isomeric mixture). Stannous reduction of $^{99m}$TcO$_4$- under basic conditions in the presence of either the LL or DD isomers produced a single radiochemical species, $^{99m}$Tc LL-EC or $^{99m}$Tc DD-EC, respectively, in greater than 90% yield. Labeling of the isomeric mixture gave a mixture of $^{99m}$Tc EC products. Two $^{99m}$Tc EC peaks were resolved by HPLC in an approximate ratio of 1:1. For both buffer systems, the first eluting peak was assigned as $^{99m}$Tc DL-EC since the second peak corresponded to the retention volume of pure $^{99m}$Tc LL-EC and $^{99m}$Tc-DD-EC. For isomeric mixtures, only the $^{99m}$Tc DL-EC peak was collected.

A.2. Preparation of $^{99m}$Tc Labeled CEMA

L-CEMA or D-CEMA (approximately 1 mg) was dissolved in 1N NaOH (100 µl). The resulting solution was highly basic (pH 12) and under basic reaction conditions the yield of the syn isomer was maximized. To maximize the yield of the anti isomer, the pH was adjusted with 1N HCl to pH 7. Freshly prepared stannous chloride solution (4 mM, 0.02 M HCl, 100 µl) and [$^{99m}$Tc] sodium pertechnetate in generator saline (0.25 ml) were added to the solution. The solution was heated at 100° C. for 15 minutes. The high pH solution was neutralized with 1N HCl (approximately 100 µl). The $^{99m}$Tc complexes were isolated by reverse phase HPLC; Beckman Ultrasphere column; mobile phase 6% 0.01 M NaH$_2$PO$_4$, pH 6.5, 1 ml/min; radiometric detection. The first (anti) or second (syn) peak was collected and used for evaluation in rat biodistribution studies, and extraction efficiency, renal clearance and plasma protein binding experiments. The biodistribution results are presented in Table 3.

TABLE 3

Biodistribution Results for $^{99m}$TcO(CEMA) Isomers*

| | Kidney | Bladder | Liver | Bowel | Carcass |
|---|---|---|---|---|---|
| anti-L-CEMA | 9 ± 2 | 72 ± 2 | 2 ± 0 | 8 ± 2 | 9 ± 1 |
| syn-L-CEMA | 7 ± 2 | 72 ± 2 | 2 ± 1 | 3 ± 1 | 15 ± 1 |
| anti-D-CEMA | 5 ± 1 | 67 ± 3 | 3 ± 1 | 10 ± 2 | 14 ± 1 |
| syn-D-CEMA | 3 ± 1 | 75 ± 2 | 4 ± 2 | 4 ± 1 | 14 ± 1 |

*Percent organ activity 30 minutes post injection; >2% in the heart, lung and spleen; n = 3.

B. General Procedure for the Formation of Metal Chelates with Monothiourea (MTU)-Based Ligands Interaction of an MTU ligand with a nuclide-containing precursor comprises the steps of deprotection of thiols in trifluoroacetic acid with triethylsilane followed by a ligand exchange reaction with a Re(V)O precursor molecule to yield a neutral ReO(MTU) chelate. This general procedure is applicable to nuclides including, but not limited to, Tc, Re, Cd, Pb, Zn, Hg, Ag, Au, Ga, Pt, Pd, Rh, Cr and V. This general procedure is exemplified in the preparation of representative metal chelates as described below.

B.1. Preparation of Re(V)O-ATU Complexes with TATU-Phe, TATU-PhOCH$_3$, TATU-PhCl, TATU-CH$_3$ and TATU-(Me)$_2$ To a stirred solution of a ligand (e.g., TATU-Phe, TATU-PhOCH$_3$, TATU-PhCl, and TATU-CH$_3$) (0.7 mmol) in MeOH (40 ml) was added 1N NaOAc in MeOH (8 ml) followed by solid ReOCl$_3$(Me$_2$S)(OPPh$_3$) (0.75). The reaction mixture was heated to 80° C. for two hours and then cooled to room temperature. The mixture was diluted with EtOAc (50 ml), washed three times with water, and dried over MgSO$_4$. Concentration of the organic layer was followed by chromatography (silica gel, 1–10% MeOH/CHCl$_3$), and then by crystallization from EtOH to give analytically pure samples of Re(V)O-TATU-Phe, Re(V)O-TATU-PhOCH$_3$, Re(M)O-TATU-PhCl and Re(V)O-TATU-CH$_3$, respectively.

Re(V)O-TATU-(Me)$_2$ was prepared in a similar manner, but from the TATU-(Me)$_2$ ligand (0.05 g, 0.23 mmol) and ReO$_2$I(PPh$_3$) (0.196 g, 0.23 mmol). Red needles were obtained in 58% yield from EtOH.

B.2. General Preparation of $^{99m}$Tc Labeled MTU

The MTU ligand (approximately 1 mg) was dissolved in 1N NaOH (100 µl). Freshly prepared stannous chloride solution (4 mM, 0.02 M HCl, 100 µl) and [$^{99m}$Tc] sodium pertechnetate in generator saline (0.25 ml) were added to the solution. The solution was allowed to stand at room temperature for 15–60 minutes or was heated at 100° C. for 10 minutes followed by neutralization of the solution with 1N HCl (approximately 100 µl). The $^{99m}$Tc complexes were isolated by reverse phase HPLC; Beckman Ultrasphere column; mobile phase-aqueous ethanol solutions with 0.01 M NaH$_2$PO$_4$, pH 6.5 or 7.0, 1 ml/min; radiometric detection. The major peak was collected and used for evaluation in rat biodistribution studies, as shown in Table 4.

TABLE 4

Biodistribution Results of $^{99m}$TcO(TPG$_2$)R = CH$_2$COOH in Rats.

| | Percent of Injected Dose | |
|---|---|---|
| Tissue | 10 minutes* | 60 minutes* |
| Blood | 3.4 ± 0.3 | 0.4 ± 0.1 |
| Kidney | 7.8 ± 1.2 | 1.2 ± 0.5 |
| Urine | 34.7 ± 3.2 | 50.9 ± 14.4 |
| Liver | 7.1 ± 0.5 | 0.9 ± 0.3 |
| Bowel | 5.4 ± 2.3 | 12.2 ± 4.2 |

*Time after injection.

C. General Procedure for Metal Chelates with Dithiourea (DTU) Ligands

Nuclide-containing chelate complexes of dithiourea (DTU) ligands were obtained through ligand exchange reactions with nuclide-containing precursor molecules. The chemistry requires neither protection of the sulfur atoms for ligand synthesis nor deprotection prior to metal complexation. This general procedure is applicable to nuclides including, but not limited to, Tc, Re, Cd, Pb, Zn, Hg, Ag, Au, Ga, Pt, Pd, Rh, Cr and V. Specific examples of the labeling procedure for specific DTU ligands are presented below.

C.1. Preparation of Re(V)O-DTU-Ph and Re(V)O-DTU-PhOCH$_3$

To stirred solutions of ligands DTU-Ph and DTU-PhOCH$_3$ (1 mmol) in methanol (20 ml) was added 1 N NaOAc in methanol (10 ml, 10 mmol) followed by solid ReOCl₃(Me₂S)(OPPh₃) (1 mmol). The reaction mixture was heated at reflux for two hours, at which time the green color of the starting metal compound had been replaced by a brownish-orange color. After being cooled to room temperature, the reaction mixture, diluted with ethyl acetate (50 ml), was washed with water. The organic layer was separated, dried over MgSO₄, and concentrated in vacuo. Purification by column chromatography (silica gel, CHCl₃/MeOH, up to 15% MeOH) was followed by crystallization from ethanol to give Re(V)O-DTU-Ph and Re(V)O-DTU-PhOCH₃, respectively, as analytically pure samples.

C.2. Preparation of ReMO-DTU-CH₃

To a solution of DTU-CH₃ (0.15 g, 0.68 mmol) and ReO₂I(PPh₃)₂ (0.59 g, 0.68 mmol) in ethanol (20 ml) was heated at 60° C. for 15 minutes with a few drops of 2 N NaOH(pH~8). After cooling, the reaction mixture was left overnight in the refrigerator. The red crystalline product which formed was collected, washed with EtOH and CHCl₃, and dried. The crude product was purified by column chromatography (silica gel, CHCl3/MeOH, 10:1) to give 0.12 g (42%) of Re(V)O-DTU-CH₃.

Example 5

Biological Studies

5.A. Biodistribution Studies

Tracheostomy was performed in an anesthetized rat and the left jugular vein was cannulated with one piece of PE-50 tubing for injection of the $^{99m}$Tc radiopharmaceutical. The bladder was catheterized utilizing heat flared PE-50 tubing for urine collection. A bolus injection of the radiopharmaceutical (400–500 μCi/0.25 ml) was given and the rat was imaged (1 frame/10 s) for 22 minutes (130 frames) using a gamma camera. Each animal was sacrificed at the conclusion of the dynamic study and simultaneous static images of the isolated lungs, heart, liver, spleen, stomach, kidneys, bowel and bladder with urine were acquired as well as a static image of the rat carcass without the organs. Total counts for the injected dose were determined from the sum of the isolated organ counts and the carcass counts decay corrected to the time of organ imaging. Regions of interest were drawn around each organ to determine the percent injected dose in each organ.

Clearance was determined by averaging three clearances based on three successive 10 minute urine collections. Clearance=UV/P where U is the urine concentration, V is the urine volume, and P is the plasma concentration. To measure extraction efficiency (EE), a left renal venous blood (0.5 ml) sample was obtained followed by a 3-ml carotid arterial sample. Both blood samples were centrifuged within 5 minutes to obtain a plasma sample. The extraction efficiency was calculated by measuring the difference between the arterial and venous blood sample: EE=(arterial concentration—venous concentrationlarterial concentration). Plasma protein binding (PPB) was determined by ultracentrifugation (Centrifree, Amicon, Inc., Beverly, Mass., micropartition system) of 1 ml arterial plasma. PPB=[1.0-(ultrafiltrate concentration/plasma concentration)]×100.

5.B. Metabolism Studies

Rats were prepared according to the procedure described for the biodistribution studies. A bolus injection of the radiopharmaceutical (1–2 mCi) was given and the urine was collected for 30 minutes. The urine was centrifuged to settle any particulates and analyzed by HPLC alone and with purified complex added. Each $^{99m}$Tc EC complex was tested in two rats.

5.C. Normal Volunteer Studies $^{99m}$Tc LL-EC, DD-EC and DL-EC were each evaluated in three normal male volunteers. The HPLC purified complexes and phosphate-buffered saline (pH 7.0) were passed through a SEP-PAK Plus C18 cartridge (primed with 1 ml ethanol) and a sterile Millex-GS 0.22 μm filter unit into a sterile, pyrogen-free empty vial. The final concentration was ~2.0 mCi/2.5 ml and the final pH ranged from 5.7 to 7.4. Test samples of each complex were sterile and pyrogen free. Approximately 2 mCi of each $^{99m}$Tc complex were coinjected with 200 μCi of I-131 OIH and plasma samples were obtained at 5, 10, 15, 20, 30 45, 60 and 90 minutes post injection. The plasma clearances of 1–131 OIH and each EC complex were determined using the single injection, two-compartment model of Sapirstein et al., (1955) Am. J. Physiol. 181: 330–336. The volunteers voided at 30, 90 and 180 minutes post injection to determine the percent dose in the urine at each time period. A urine sample from the 30 minute urine collection was obtained for HPLC analysis from one of the normal volunteers and analyzed for each complex. One volunteer was imaged with each complex using a simultaneous acquisition with a 20% window centered over the 363 KeV photopeak of I-131 and a second 20% window over the 140 KeV photopeak of $^{99m}$Tc. Data were acquired in a 128×128 matrix using a three phase dynamic acquisition: phase 1 consisted of 24 two second frames, phase 2 consisted of 16 fifteen second frames and phase 3 consisted of 40 thirty second frames. Data were acquired using a general Electric (Milwaukee, Wis.) Star-Cam computer fitted with a high energy collimator. All studies were performed with the approval of the Human Investigations Committee and a signed consent form was obtained.

5.D. Statistical Analysis

The statistical analysis was based on an analysis of variance (ANOVA) and the independent t-test. A p≦0.02 was considered to be significant. Data with an n≦3 were not analyzed.

We claim:

1. A metal chelate based on a cysteinylethylene structure having the general formula

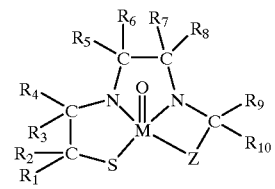

wherein $R_1$–$R_{10}$ are individually selected from the group consisting of hydrogen, a straight or branched, unsubstituted or substituted alkyl having C=1–4, and ACOOH wherein A is a straight or branched, unsubstituted or substituted alkyl group having C=0–4;

$R_3$ together with $R_4$, $R_5$ together with $R_6$, $R_7$ together with $R_8$, and $R_9$ together with $R_{10}$ may form an oxygen atom;

Z is selected from the group consisting of

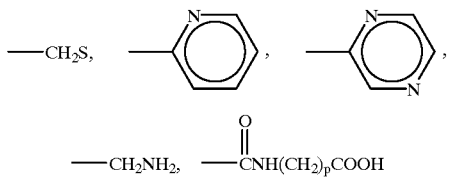

where p=1–3, and
—CH$_2$NH(CH$_2$)$_p$COOH where p=1–3; and

M is selected from the group consisting of technetium (Tc), rhenium (Re), cadmium (Cd), lead (Pb), zinc (Zn), mercury (Hg), silver (Ag), gold (Au), gallium (Ga), platinum (Pt), palladium (Pd), rhodium (Rh), chromium (Cr) and vanadium (V);

with the provision that
(a) at least one of R$_1$–R$_{10}$ is ACOOH or, together with one other R group, forms an oxygen atom; and/or
(b) only one of R$_1$, R$_2$, R$_3$ or R$_4$ and R$_5$, R$_6$, R$_7$ or R$_8$ and R$_9$ or R$_{10}$ is a straight or branched, unsubstituted or substituted alkyl of C$_3$ or C$_4$ or is an ACOOH wherein A is a straight or branched, unsubstituted or substituted alkyl group having C=0–4.

2. The metal chelate of claim 1 wherein M is technetium-99m or rhenium.

3. The metal chelate of claim 2 selected from the group consisting of L-cysteinylethylenemercaptoacetamide (L-CEMA), D-cysteinylethylenemercaptoacetamide (D-CEMA), L-cysteinyl-ethylenepyridine carboxamide (L-CEPIC), D-cysteinyl-ethylenepyridine carboxamide (D-CEPIC), L-cysteinyl-ethylenepyrazine carboxamide (L-CEPZ), D-cysteinyl-ethylenepyrazine carboxamide (D-CEPZ), cysteinylethylene-glycine (CEG), thiodiacetamide-amine-CH$_3$ (TDAA-CH$_3$), thiodiacetamide-amine-CH$_2$CH$_2$COOH (TDAA-CH$_2$CH$_2$COOH) and cysteinylacetylglycylglycine (CAG$_2$).

4. The metal chelate of claim 3 that is the D- or L-isomer of cysteinylethylenemercaptoacetamide (CEMA) or the D- or L-isomer of cysteinylethylenepyridine carboxamide (CEPIC).

5. A composition suitable for examination of renal function, said composition comprising a metal chelate based on a cysteinylethylene structure having the general formula as claimed in claim 1 and a pharmaceutically acceptable carrier.

6. The composition of claim 5 wherein said metal chelate is a chelate of technetium-99m or rhenium.

7. The composition of claim 6 wherein said metal chelate is selected from the group consisting of L-cysteinylethylene-mercaptoacetamide (L-CEMA), D-cysteinylethylenemercapto-acetamide (D-CEMA), L-cysteinylethylenepyridine carboxamide (L-CEPIC), D-cysteinylethylenepyridine carboxamide (D-CEPIC), L-cysteinylethylenepyrazine carboxamide (L-CEPZ), D-cysteinylethylenepyrazine carboxamide (D-CEPZ), cysteinylethyleneglycine (CEG), thiodiacetamide-amine-CH$_3$ (TDAA-CH$_3$), thiodiacetamide-amine-CH$_2$CH$_2$COOH TDAA-CH$_2$CH$_2$COOH) and cysteinylacetylglycylglycine (CAG$_2$).

8. The composition of claim 6 wherein said metal chelate is the D- or L-isomer of cysteinylethylenemercaptoacetamide (CEMA) or the D- or L-isomer of cysteinylethylenepyridine carboxamide (CEPIC).

9. A compound useful in forming a metal chelate based on a cysteinylethylene structure, said compound comprising a ligand having the formula

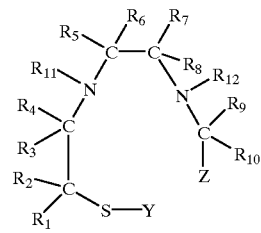

wherein
R$_1$–R$_{12}$ are individually selected from the group consisting of hydrogen, a straight or branched, unsubstituted or substituted alkyl having C=1–4, a hydroxy-alkyl, and ACOOH wherein A is a straight or branched, unsubstituted or substituted alkyl group having C=0–4;

R$_3$ together with R$_4$, R$_5$ together with R$_6$, R$_7$ together with R$_8$, and R$_9$ together with R$_{10}$ may form an oxygen atom;

Z is selected from the group consisting of

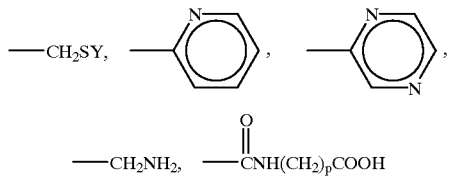

where p=1–3, and
—CH$_2$NH(CH$_2$)$_p$COOH where p=1–3; and

Y is a hydrogen atom or a suitable protecting group;

with the provision that
(a) at least one of R$_1$–R$_{10}$ is ACOOH or, together with one other R group, forms an oxygen atom; and/or
(b) only one of R$_1$, R$_2$, R$_3$ or R$_4$ and R$_5$, R$_6$, R$_7$ or R$_8$ and R$_9$ or R$_{10}$ is a straight or branched, unsubstituted or substituted alkyl of C$_3$ or C$_4$, a hydroxy-alkyl, or is an ACOOH wherein A is a straight or branched, unsubstituted or substituted alkyl group having C=0–4.

10. The compound of claim 9 wherein said ligand is selected from the group consisting of L-cysteinylethylenemercapto-acetamide (L-CEMA), D-cysteinylethylenemercaptoacetamide (D-CEMA), L-cysteinylethylenepyridine carboxamide (L-CEPIC), D-cysteinylethylenepyridine carboxamide (D-CEPIC), L-cysteinylethylenepyrazine carboxamide (L-CEPZ), D-cysteinylethylenepyrazine carboxamide (D-CEPZ), cysteinylethylene-glycine (CEG), thiodiacetamide-amine-CH$_3$ (TDAA-CH$_3$), thiodiacetamide-amine-CH$_2$CH$_2$COOH (TDAA-CH$_2$CH$_2$COOH), and cysteinylacetylglycylglycine (CAG$_2$).

11. The compound of claim 9 wherein said ligand is the D- or L-isomer of cysteinethylenemercaptoacetamide (CEMA) or the D- or L-isomer of cysteinylethylenepyridine carboxamide (CEPIC).

12. A kit for formation of a $^{99m}$Tc-chelate suitable for examination of renal function, said kit comprising
a ligand based on a cysteinylethylene structure and having the general formula

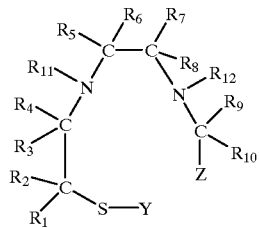

wherein

R$_1$–R$_{12}$ are individually selected from the group consisting of hydrogen, a straight or branched, unsubstituted or substituted alkyl having C=1–4, a hydroxy-alkyl, and ACOOH wherein A is a straight or branched, unsubstituted or substituted alkyl group having C=0–4;

R$_3$ together with R$_4$, R$_5$ together with R$_6$, R$_7$ together with R$_8$, and R$_9$ together with R$_{10}$ may form an oxygen atom;

Z is selected from the group consisting of

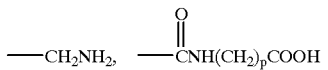

where p=1–3, and

—CH$_2$NH(CH$_2$)$_p$COOH where p=1–3; and

Y is a hydrogen atom or a suitable protecting group; with the provision that (a) at least one of R$_1$–R$_{10}$ is ACOOH or, together with one other R group, forms an oxygen atom; and/or (b) only one of R$_1$, R$_2$, R$_3$ or R$_4$ and R$_5$, R$_6$, R$_7$ or R$_8$ and R$_9$ or R$_{10}$ is a straight or branched, unsubstituted or substituted alkyl of C$_3$ or C$_4$, a hydroxy-alkyl, or is an ACOOH wherein A is a straight or branched, unsubstituted or substituted alkyl group having C=0–4;

and a reducing agent.

13. The kit of claim 12 further comprising a stabilizing agent and/or a chelating agent.

14. A method of performing a renal function examination in a patient or control subject comprising the step of administering a radiopharmaceutical composition comprising $^{99m}$Tc- D,D-ethylenedicysteine ($^{99m}$Tc D,D-EC) in a quantity of between 0.1 and 30 mCi per 70 kg of body weight.

* * * * *

UNITED STATES PATENT AND TRADEMARK OFFICE
CERTIFICATE OF CORRECTION

PATENT NO. : 5,986,074

DATED : November 16, 1999

INVENTOR(S) : Marzilli et al.

It is certified that error appears in the above-identified patent and that said Letters Patent is hereby corrected as shown below:

In column 9, line 51, please delete "—(CH)$_p$COOH" and replace with -- —(CH$_2$)$_p$COOH --.

In column 9, line 55, please insert --or R$_{10}$-- following "R$_9$".

In column 11, line 34, please delete "C=14" and replace with --C=1-4--.

In column 12, line 8, please delete " —CH$_2$NH(CH)$_p$COOH" and replace with -- —CH$_2$NH(CH$_2$)$_p$COOH--.

In column 13, line 55, please insert --1,-- following "n=0 or".

In column 13, line 63, please delete "R." and replace with --R$_5$--.

In column 14, line 29, please delete "—(CH)$_p$COOH" and replace with -- —(CH$_2$)$_p$COOH --.

In column 14, line 48, please delete "TATU-PhOCH." and replace with --TATU-PhOCH$_3$--.

In column 17, line 51, please delete "R$_r$" and replace with --R$_1$--.

In column 26, line 10, please insert "mmol" following "0.75".

In column 26, line 18, please delete "Re(M)O-TATU-PhCl" and replace with --Re(V)O-TATU-PhCl--.

In column 27, line 12, please delete "ReMO-DTU-CH$_3$" and replace with --Re(V)O-DTU-CH$_3$--

In column 27, line 54, please delete "concentrationlarterial" and replace with --concentration/arterial--.

In claim 7, column 29, line 60, please insert --(-- prior to "TDAA".

UNITED STATES PATENT AND TRADEMARK OFFICE
CERTIFICATE OF CORRECTION

Page 2 of 3

PATENT NO. : 5,986,074

DATED : November 16, 1999

INVENTOR(S) : Marzilli et al.

It is certified that error appears in the above-identified patent and that said Letters Patent is hereby corrected as shown below:

In item [63], please delete "abandoned" and replace with --now patent 5,955,053, September 21, 1999--.

At column 1, line 6, please delete "abandoned" and replace with --now patent 5,955,053, September 21, 1999--.

In column 4, line 32, please delete "TDM" and replace with --TDAA--.

In column 6, line 1, please delete "hippunc" and replace with --hippuric--.

In column 6, line 18, please delete "(III)" and replace with --(III)--.

In column 8, line 27, please delete "R" and replace with --$R_6$--.

In column 9, at about line 6, please delete the structure

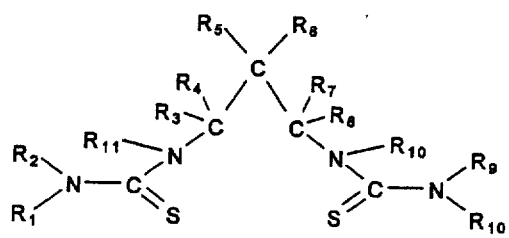

and replace with the structure

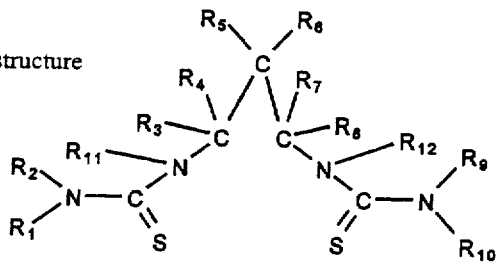

UNITED STATES PATENT AND TRADEMARK OFFICE
CERTIFICATE OF CORRECTION

Page 3 of 3

PATENT NO. : 5,986,074
DATED : November 16, 1999
INVENTOR(S) : Marzilli, et al.

It is certified that error appears in the above-identified patent and that said Letters Patent is hereby corrected as shown below:

and replace with the structure

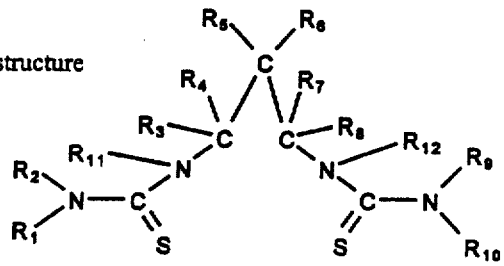

Signed and Sealed this

Second Day of January, 2001

Attest:

Q. TODD DICKINSON

*Attesting Officer*  Commissioner of Patents and Trademarks